United States Patent [19]

Ohtsuka et al.

[11] Patent Number: 5,013,830
[45] Date of Patent: May 7, 1991

[54] COMPOUNDS FOR THE CLEAVAGE AT A SPECIFIC POSITION OF RNA, OLIGOMERS EMPLOYED FOR THE FORMATION OF SAID COMPOUNDS, AND STARTING MATERIALS FOR THE SYNTHESIS OF SAID OLIGOMERS

[75] Inventors: Eiko Ohtsuka; Hideo Inoue, both of Sappro; Hirokazu Morisawa, Kawasaki; Susumu Shibahara, Kawasaki; Sachiko Mukai, Kawasaki; Tohru Nishihara, Kurashiki, all of Japan

[73] Assignee: Ajinomoto Co., Inc., Tokyo, Japan

[21] Appl. No.: 478,741

[22] Filed: Feb. 12, 1990

Related U.S. Application Data

[63] Continuation of Ser. No. 92,198, Sep. 2, 1987, abandoned.

[30] Foreign Application Priority Data

Sep. 8, 1986 [JP] Japan ................. 61-211157
Jan. 23, 1987 [JP] Japan ................. 62-13726

[51] Int. Cl.$^5$ ............................ C07H 21/00
[52] U.S. Cl. ....................... 536/27; 536/28; 536/29
[58] Field of Search ............... 536/27, 28, 29

[56] References Cited

U.S. PATENT DOCUMENTS

| | | | |
|---|---|---|---|
| 4,401,796 | 8/1983 | Itakura | 536/28 |
| 4,415,732 | 11/1983 | Caruthers et al. | 536/28 |
| 4,503,151 | 3/1985 | Paddock | 536/28 |
| 4,661,450 | 4/1987 | Kempe et al. | 536/27 |
| 4,725,677 | 2/1988 | Koster et al. | 536/28 |

FOREIGN PATENT DOCUMENTS

| | | | |
|---|---|---|---|
| 0090789 | 3/1982 | European Pat. Off. | 536/23 |
| 56-44400 | 2/1982 | Japan | 536/23 |
| 0004199 | 1/1985 | Japan | 536/29 |

OTHER PUBLICATIONS

Hideo Inoue, et al, Nucleic Acids Research, Symposium Series No. 16, 1985.
Koster, H. et al. N—acyl Protecting Groups for Deoxynucleosides. A Quantitative and Comparative Study (1981).

*Primary Examiner*—John W. Rollins
*Assistant Examiner*—James O. Wilson
*Attorney, Agent, or Firm*—Oblon, Spivak, McClelland, Maier & Neustadt

[57] ABSTRACT

There is disclosed a compound having a double chain which is composed of an RNA (+chain) and a complementary DNA (−chain), wherein a portion of the DNA (−chain) has been replaced by an RNA or a derivative thereof, and wherein, when the compound is subjected to the action of an enzyme having a ribonuclease H activity, it is possible to preferentially cleave the RNA (+chain) in a position corresponding to the unsubstituted portion of the DNA (−chain). The compound can thus be used for the preferential cleavage of a phosphodiester bond in a specific position of RNA. Accordingly, the invention provides a useful means for preparing, for instance, a deletion mutant. There is also disclosed a mixed oligomer which comprises an oligomer of RNA or a derivative thereof and a DNA oligomer, wherein the RNA oligomer or a derivative thereof is conjugated to the DNA oligomer via a phosphate diester linkage between the 5′-hydroxyl group and the 3′-hydroxyl group in the ribose or deoxyribose moiety. There is further disclosed a nucleoside derivative of a given general formula for use as a starting material.

17 Claims, 10 Drawing Sheets

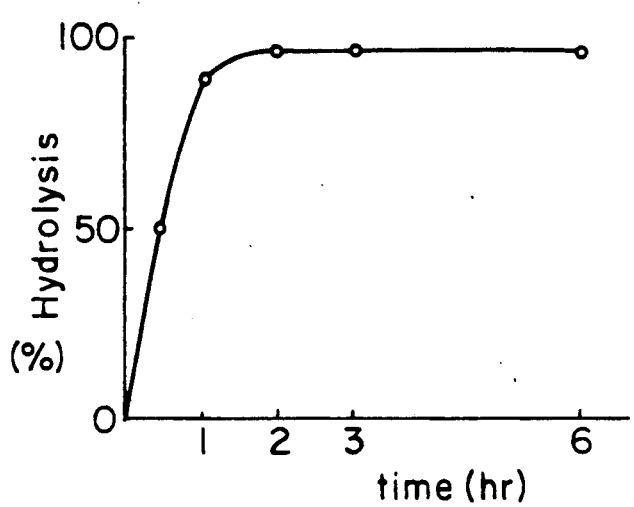
Fig.2.
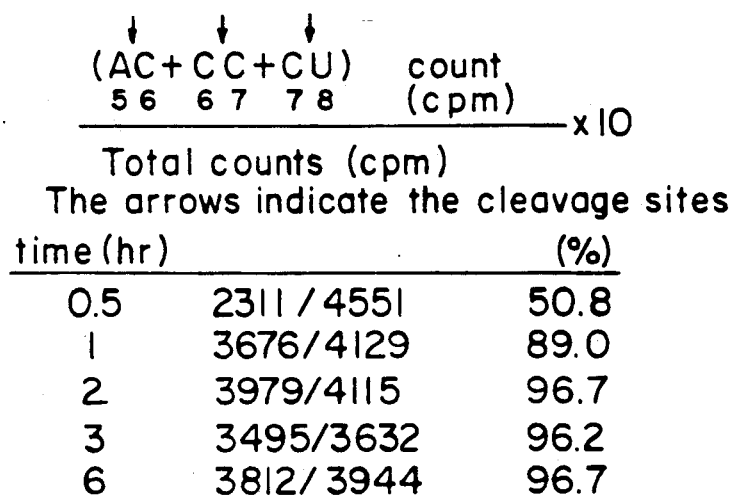
$$\frac{(AC + CC + CU) \text{ count (cpm)}}{\text{Total counts (cpm)}} \times 10$$
The arrows indicate the cleavage sites
| time (hr) | | (%) |
|---|---|---|
| 0.5 | 2311/4551 | 50.8 |
| 1 | 3676/4129 | 89.0 |
| 2 | 3979/4115 | 96.7 |
| 3 | 3495/3632 | 96.2 |
| 6 | 3812/3944 | 96.7 |
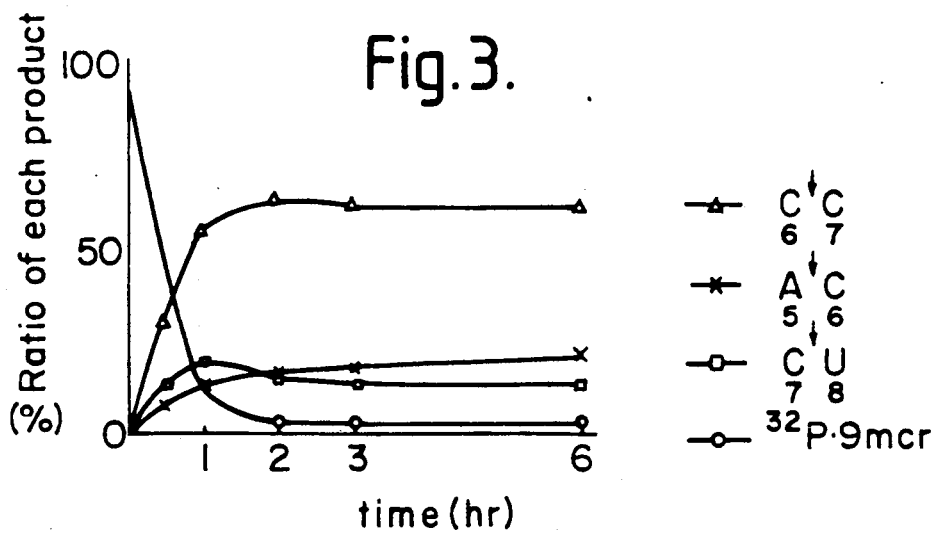
Fig.3.

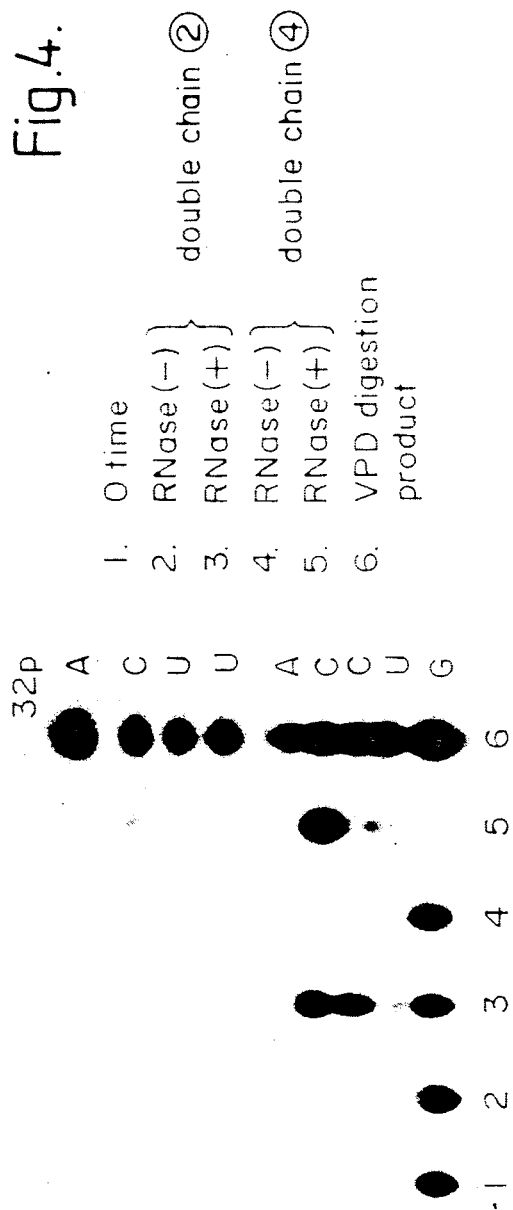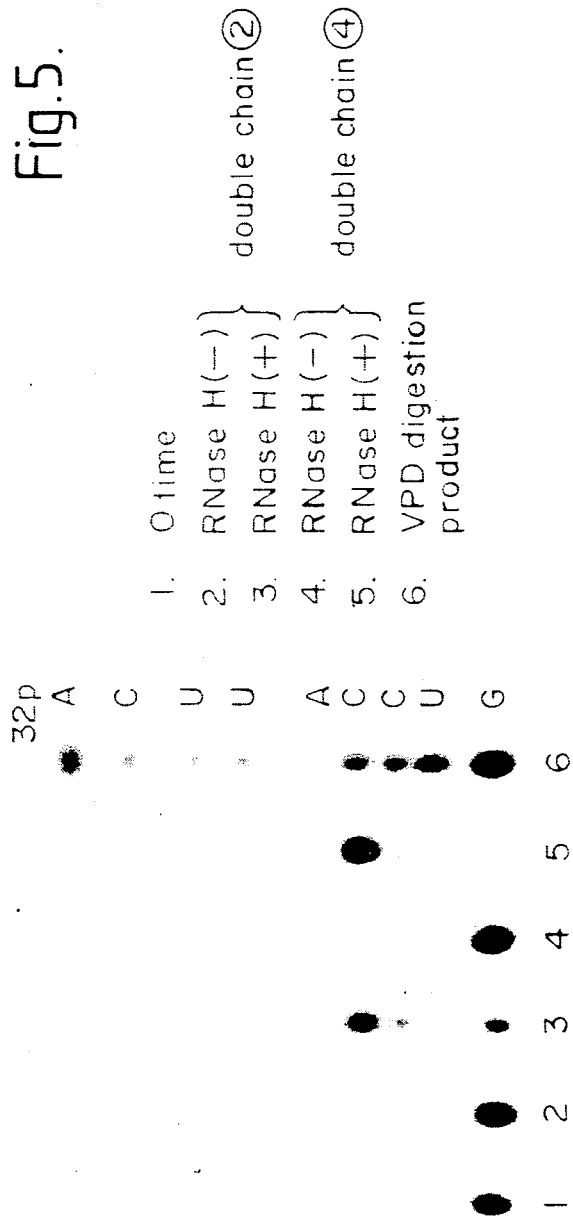

(*) Lane 2: The synthetic
DNA 7 which was mentioned
in the scheme of text,
was used lane 1. intact
lane 2. XXI 25eq.
lane 3. XXI 250eq.
lane 4. XXI 2500eq.
lane 5. XXIV 25eq.
lane 6. XXIV 250eq.
lane 7. XXIV 2500eq.
lane 8. XIX 25eq.
lane 9. XIX 250eq.
lane 10. XIX 2500eq.
lane 11. XVIII 25eq.
lane 12. XVIII 250eq.
lane 13. XVIII 2500eq.
lane 14. XVII 25eq.
lane 15. XVII 250eq.
lane 16. XVII 2500eq.
lane 17. alkaline
lane 18. RNase $T_1$
lane 19. RNase $U_2$
lane 20. RNase Phy M The cleavage products by RNaseH
(The effect of using different amounts of
mixed oligomers)

Fig. 12.
Autoradiograph of the acidic paper electrophoresis of the complete digestion products with Nuclease P1
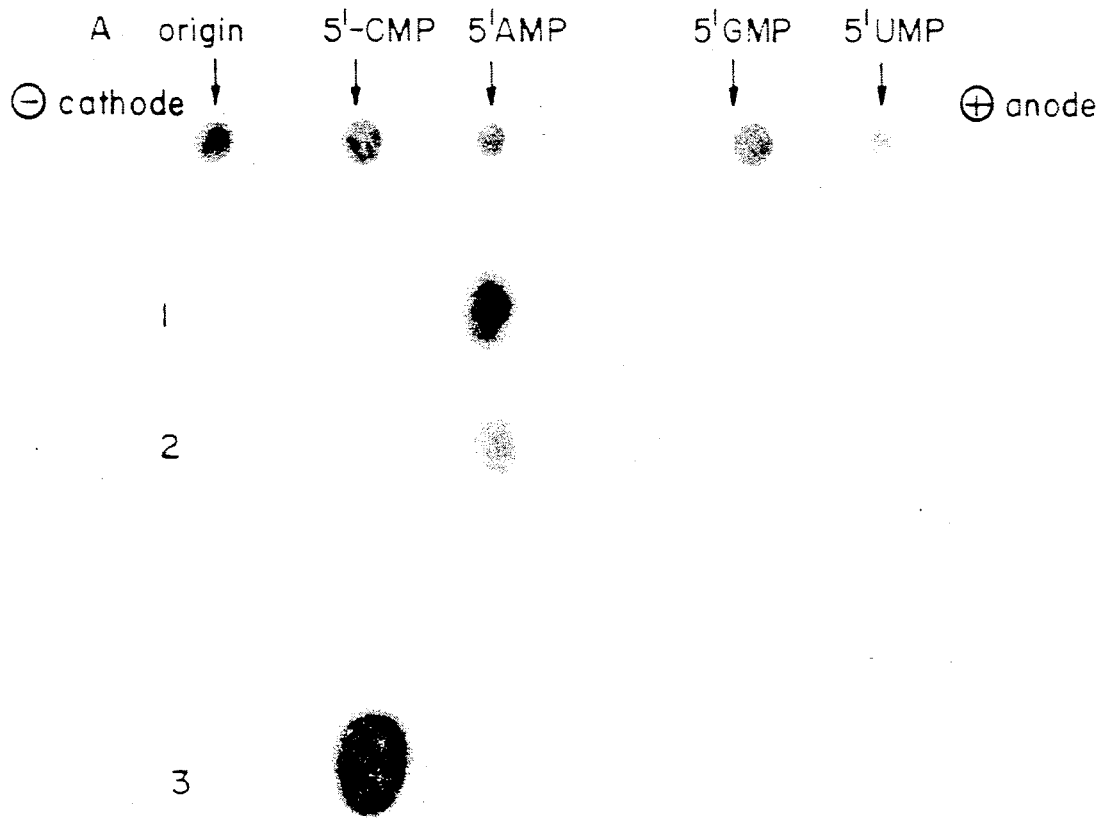
1, 2: The cleavage products of WS'-S'(+)RNA, (XXIV), using 5'CmUmCGAAGmUm3'
3: The digestion product of yeast 5S'RNA which was 3'-end labeled by 32pCp.
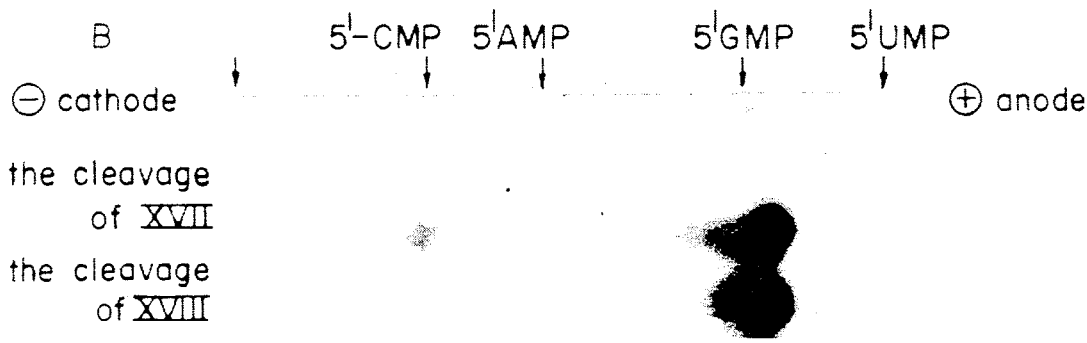

COMPOUNDS FOR THE CLEAVAGE AT A SPECIFIC POSITION OF RNA, OLIGOMERS EMPLOYED FOR THE FORMATION OF SAID COMPOUNDS, AND STARTING MATERIALS FOR THE SYNTHESIS OF SAID OLIGOMERS

This application is a continuation of application Ser. No. 07/092,198, filed on Sept. 2, 1987, now abandoned.

BACKGROUND OF THE INVENTION

1. Field of the Invention

The present invention relates to a novel compound which can be used for the preferential cleavage of a phosphodiester bond in a specific position of RNA. Thus, the invention provides a useful means for preparing, for instance, a deletion mutant. Thus, the invention broadly provides an effective means for treating RNA in the case of molecular biological experiments directed, for example, to the mass production of useful proteins, to the improvement of the properties of proteins, to studies of the relationship between the structure and the function of proteins, to the development of methods of eliminating toxic components in toxic RNA viruses, to the development of methods for treating diseases caused by toxic viruses, and to various studies concerning molecular biological science.

The invention relates also to oligomers to be used in said novel compound, and to starting materials for the syntheses of said oligomers.

A method for the preferential cleavage of a phosphodiester bond at a desired position of an RNA molecule will serve as a useful means for studying the structure and function of a functional RNA molecule. For instance, such a method may be employed in studies of the structure and stability of m-RNA which codes a useful protein or an enzyme protein, in relation to the translation rate. It is also possible to use such a method in research into the molecular structure and function of RNA virus genes which are harmful to animals and plants.

2. Description of the Prior Art

There are a number of known methods for the cleavage of a phosphodiester bond in an RNA molecule. One of these known methods comprises using a basespecific natural ribonuclease such as $RNaseT_1$, $RNaseU_2$ or the like. Another method comprises forming a double chain from an RNA molecule and a complementary DNA, and cleaving the RNA strand in the double chain by the use of RNaseH, i.e. ribonuclease H (H. Donis-Keller, Nucleic Acids Res., 7, 179, 1979). In the case of the former method, it is rather difficult to cleave the linkage only in the desired position of the molecule. In other words, in the case of the former method, the base-specific cleavage may occur at many sites of the molecule, so that the method is widely employed for the determination of the base sequence in an RNA molecule (H. Donis-Keller et al, Nucleic Acid Res., 4, 2527, 1977). In the case of the latter method, when a long DNA chain is employed, the cleavage will occur at various sites, and when a short DNA chain consisting of, for instance, 4 or 6 bases is employed, a preferential cleavage will be expected. However, if the DNA chain is short, such a short DNA chain will form a double chain at various positions without any substantial positional preference. Thus, according to these known methods, it is virtually impossible to preferentially cleave the phosphodiester bond in a desired position of an RNA molecule.

It is desired in the field of biological science to develop a novel method for the preferential cleavage of phosphodiester bond in a desired position of an RNA molecule without any limitation on the chain length and the base arrangement of the RNA. It is apparent that such a novel method will serve as a useful means in studies on the structure and the function of a functional RNA. Such studies are important, for instance, for the development of processes for the mass production of useful proteins, and of methods of improving the properties of proteins, and for the development of methods for the detoxication of harmful RNA viruses and methods for effectively treating diseases caused by such viruses.

SUMMARY OF THE INVENTION

It is known that an 2'-O-methyl RNA can form a stable double chain with an RNA molecule having a complementary sequence (H. Inoue et al, Nucleic Acids Symposium Series, No. 16, 165, 1985) (1).

We have made many studies on RNA and have now found, on the basis of the above-mentioned known fact, that the RNA chain and the 2'-O-methyl RNA chain, which are the constituents of the double chain, are not cleaved under the influence of RNaseH.

Furthermore, we have found that a mixed oligomer, which is a 2'-O-methyl RNA linked to DNA, can be easily produced; that a double chain may be formed from said mixed oligomer and a complementary RNA molecule; and that, when the double chain is treated with an RNaseH, the DNA portion of the mixed oligomer serves as a position specifically recognized by the RNaseH, notwithstanding the fact that one or both sides of the DNA portion is connected to the 2'-O-methyl RNA, so that it is possible to preferentially cleave the phosphodiester bond in the position of the RNA corresponding to the DNA oligomer portion.

Accordingly, the invention relates to a compound for cleaving a chemical bond in a specific position of RNA, which compound has a double chain which is composed of an RNA (+chain) and a complementary DNA (−chain), wherein a portion of the DNA (−chain) has been replaced by an RNA or a derivative thereof, and wherein, when the compound is subjected to the action of an enzyme having ribonuclease H activity, then a preferential cleavage occurs in a position of the RNA (+chain) corresponding to the unsubstituted portion of the DNA (−chain).

The invention also provides a mixed oligomer which comprises an oligomer of RNA or a derivative thereof and a DNA oligomer, wherein the RNA oligomer or derivative thereof is conjugated to the DNA oligomer via a phosphodiester linkage between the 5'-hydroxyl group and the 3'-hydroxyl group in the ribose or deoxyribose moiety.

The invention further provides a nucleoside derivative of the general formula:

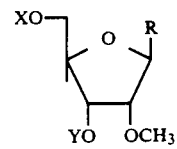

wherein X represents a monomethoxy-trityl or dimethoxytrityl radical, Y represents —P(OCH$_3$)—N—(CH(CH$_3$)$_2$)$_2$, —P(OCH$_2$CH$_2$CN)—N—(CH(CH$_3$)$_2$)$_2$, or —CO(CH$_2$)$_m$—CO—NH—(CH$_2$)$_n$—(CPG-derivative), m and n are each an integer of 1 to 10, and R represents a radical having any of the following formulae:

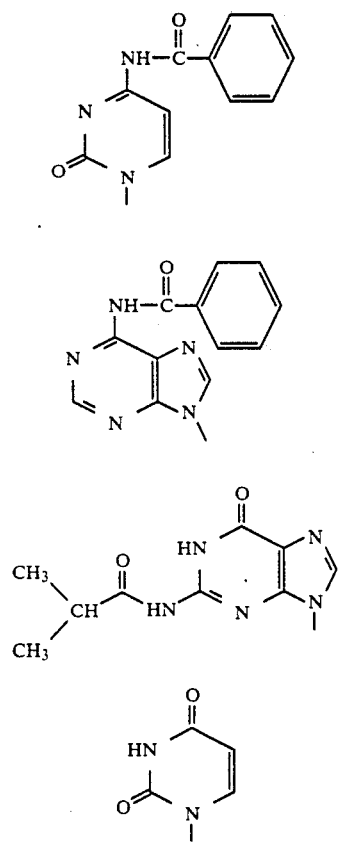

BRIEF DESCRIPTION OF THE DRAWINGS

FIG. 2 and 3 are graphs illustrating the relationship between the cleavage time and the cleavage rate of the cleaved position shown in FIG. 1.

FIGS. 4 to 9 each show a homo-chromatograph, illustrating the chain cleavage of a compound consisting of a labelled RNA oligomer, an unlabelled RNA oligomer and a complementary mixed oligomer.

FIGS. 10-1, 10-2 and 11 each show an autoradiograph, illustrating the chain cleavage process of the 3'-$^{32}$PCp-labelled WS-S(+)RNA and the mixed oligomer according to the invention.

FIGS. 12A and 12B show an autoradiographs, illustrating the analytical results of 5'-terminal base in a cleaved fragment formed by the action of RNase H shown in FIG. 10-1.

DETAILED DESCRIPTION OF THE INVENTION

Figure 1:
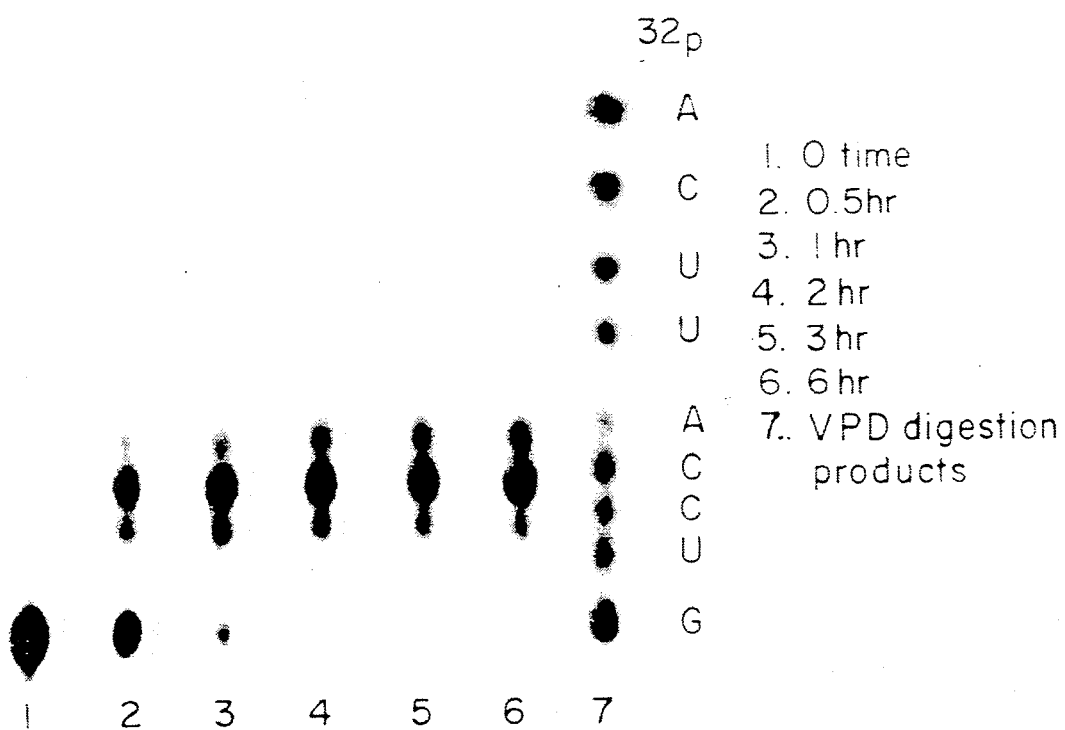
FIG. 1 shows a homo-chromatograph, illustrating the chain cleavage of a compound consisting of a labelled RNA oligomer, an unlabelled RNA oligomer and a complementary DNA oligomer according to the invention.

The compound having the double chain consisting of RNA (+chain) and a complementary DNA (—chain), are known or can be prepared in a known manner. It is unnecessary to form a double chain on the whole portion of RNA (+chain) with the aid of a DNA (—chain). In other words, a double chain may be formed only on a portion of the RNA (+chain). It is also possible to form a double chain on each of two or more portions of the RNA.

In case where a portion of DNA (—chain) is replaced by an RNA or its derivatives, "a portion of DNA (—chain)" may be a portion of the DNA molecule which is a constituent of the double chain, or if there are two or more double chain parts on the same RNA strand, "a portion of DNA (—chain)" may be the DNA molecule (—chain) present in at least one double chain.

The derivatives or RNA have a substituent on at least one 2'-hydroxyl group of the sugar moiety of RNA.

As the oligomer, wherein a portion of DNA (—chain) has been partially substituted, use may conveniently made of mixed oligomer shown below.

Such a mixed oligomer may be obtained by connecting an oligomer of RNA or of its derivative to a DNA oligomer in such a way that the 5'-hydroxyl group and the 3'-hydroxyl group of the ribose or deoxyribose portion are bonded to each other via a phosphodiester linkage.

The 2'-O-methyl RNA oligomer portion of the mixed oligomer may be prepared by any one of the following two methods. One of these methods is that described by Inoue in the publication (1). According to the method by Inoue, 2'-O-methyl-N$^4$-benzoylcytidine (compound I), 2'-O-methyl-N$^6$-benzoyladenosine (compound II), 2'-O-methyl-N$^2$-isobutyrylguanosine (compound III) and 2'-O-methyluridine (compound IV) are prepared. The 5'-hydroxyl group of each compound is protected by a dimethoxy-trityl group (-DMTr), so that compounds (Ia, IIa, IIIa, IVa) are obtained. It is possible to prepare compounds (Ib, IIb, IIIb, IVb) by introducing an ortho-chlorophenyl phosphate radical into the 3'-hydroxyl group of each of the compounds (Ia–IVa) according to a known manner (Nucleic Acids Res., 8, 5461, 1980). The preparative method shown above is hereinafter referred to as "method A".

Furthermore, the 3'-hydroxyl group of the compound (Ia, IIa, IIIa, IVa) may be treated with chlorodiisopropylamino-methoxy-phosphine or chloro-diisopropylamino-cyanoethoxy-phosphine according to a known method (Tetrahedron Lett., 24, 245, 1983, and Nucleic Acids Res., 11, 4539, 1984) to produce 3'-phosphoramidite compound (Ib$_2$, IIb$_2$, IIIb$_2$, IVb2, Ib$_3$, IIb$_3$, IIIb$_3$, IVb$_3$) ("method B"; see Examples 11 and 12).

The compounds (Ia to IVa) each may be combined via a spacer with a 1%-crosslinked polystyrene resin to form compounds (Ic$_1$, IIc$_1$, IIIc$_1$, IVc$_1$) according to a known method (Nucleic Acids Res., 8, 5507, 1980).

The compounds (Ia, IIa, IIIa, IVa) may be treated according to a known method (K. Miyoshi et al, Nucleic Acids Res., 8, 5491, 1980), wherein 3'-succinyl derivatives (Ie, IIe, IIIe, IVe) are converted to active esters (If, IIf IIIf, IVf), which are then bonded to long chain alkylamino controlled pore glass; CPG) to form compounds (Ic$_2$, IIc$_2$, IIIc$_2$, IVc$_2$) as illustrated in Example 13.

The DNA oligomer portion of the mixed oligomer may be prepared according to a known method (M. Ikehara et al, Proc. Natl. Acad. Sci. USA., 81, 5956, 1984; publication 2) by successively condensing the compounds (Id$_1$, IId$_1$, IIId$_1$, IVd$_1$) (method A).

Furthermore, it is possible to produce the DNA portion by successively bonding the compounds (Id$_2$, IId$_2$, IIId$_2$, IVd$_2$) or by successively bonding the compounds (Id$_3$, IId$_3$, IIId$_3$, IVd$_3$) according to a known manner (Science, 230, 281, 1985) as illustrated in Table 1 (method B).

For instance, the starting compound (IVc$_1$) may be successively reacted with the compounds (IIIb$_1$, IId$_1$, IId$_1$, IVd$_1$, IIId$_1$, IIIb$_1$, IIb$_1$, Ib$_1$ in this order) under the reaction conditions shown in Table 2, to form the mixed oligomer (compound V) of the formula:

3'UmGmAATGGmAmCm5'   (V)

wherein the symbols with suffix m represent O-methyl RNA, and other symbols represent DNA oligomers.

In a similar manner, the following mixed oligomers (compounds VI to VIII) may be prepared:

3'UmGmAmATGGmAmCm5'   (VI)

3'UmGmAATGGAmCm5'   (VII)

3'UmGmAmAmTGGACm5'   (VIII)

A DNA oligomer (compound IX), having the same sequence as that of the above-mentioned mixed oligomers, may be prepared according to a known method shown in the article by Ikehara et al (publication 2). A low molecular weight RNA oligomer (X), having a complementary sequence to that of the mixed oligomers (compounds V to IX), may be prepared according to a known method (S. Iwai et al. Chem. Pharm. Bull., 33, 4618, 1985; publication 3).

3'd(TGAATGGAC)5'   (IX)

5'ACUUACCUG3'   (X)

Other mixed oligomers (XI, XII) and other complementary RNA oligomers (XIII, XIV), shown below, may be prepared according to the methods described in publications 2 and 3, respectively.

3'CmAmTTCAUmAmGm5'   (XI)

3'GmUmCCAACmCmAm5'   (XII)

5'GUAAGUAUC3'   (XIII)

5'CAGGUUGGU3'   (XIV)

A high molecular weight RNAWS-S(+) (90 mer; compound XV) can be prepared by an in vitro transcription reaction using a SP6-RNA polymerase. In this process, a double chain DNA (XVI), wherein a WS-S(+) sequence is directly connected to an SP6-promoter sequence, is prepared in chemical/enzymatical manner according to the scheme shown in Table 3 in order to conduct the transcription starting from the 5'-terminal of the base arrangement of the WS-S(+)RNA.

Firstly, the DNA oligomers (1 to 9) were prepared according to a known method (Science, 230, 281, 1985), and divided into two groups. By means of a ligase reaction, the double chain DNA (XVI) was obtained. A subcloning operation of the double chain DNA (XVI) to Sph I and Sma I sites of M13 mp 19 vector was carried out, and E. coli JM 103 was subjected to a transformation operation to obtain a vector M13AJ-1 for transcription.

The synthetic double chain DNA sequence within the vector M13AJ-1 for transcription thus obtained was tested by a known M13-dideoxy method (Proc. Natl. Acad. Sci. USA., 74, 5463, 1977). It was confirmed by this test that the base sequence in question was correct.

Next, the M13AJ-1 was linearized with a restriction enzyme Sma I, and then an in vitro RNA transcription reaction was conducted with the aid of an SP6-polymerase according to a known method (Nucleic Acids Res., 12, 7035, 1984) to produce the aimed RNA WS-S(+) (XV), wherein the transcription had been exactly made starting from the 5'-terminal portion.

In order to study a cleavage reaction of the high molecular RNA WS-S(+) (XV) obtained, the following operations were carried out. At first, an experiment was conducted wherein a mixed oligomer was chemically produced according to the method B, which is rather simple as compared with the method A, and therefore widely employed in this field. The starting material used was the compound (IVc$_2$). Under the reaction conditions shown in Table 6, the compound (IVc$_2$) was successively condensed with the following compounds: IIIb$_2$, IIIb$_2$, IIIb$_2$, Ib$_2$, Ib$_2$, IIIb$_2$, IIb$_2$, IVb$_2$, Ib$_2$, IVb$_2$, IId$_2$, IIId$_2$, IIId$_2$ and Id$_2$ in this order. The crude product thus obtained was worked up in a conventional manner, so that a mixed oligomer (XVIII) was obtained as in the case of the DNA synthesis.

3'-UmGmGmGmCmCmGmAmUmCmUmAGGC-5'   (XVIII)

In a similar manner, the following mixed oligomers (XVII, XIX, XXII–XXIV) were produced.

3'-UmGmGmGmCmCmGmAmUmCmTAGGC-5'   (XVII)

3'-UmGmGmGmCmCmGmAmUmCmUmAmGGC-5'   (XIX)

3'-AGGCCmCmAmCmAmCmAm-5'   (XXII)

3'-GGCCmCmAmCmAmCmAm-5'   (XXIII)

3'-UmGmAAAGCUmCm   (XXIV)

Next, use was made of the compound (IVd$_4$) as the starting material. The compound (IVd$_4$) was successively condensed with the following compounds in this order: IId$_3$, IIId$_3$, IIId$_3$, Ib$_3$, Ib$_3$, Ib$_3$, IIb$_3$, Ib$_3$, IIb$_3$, Ib$_3$ and IIb$_3$, under the reaction conditions shown in Table 6 and Example 15, to produce a mixed oligomer (XX).

3'TAGGCmCmCmAmCmAmCmAm5'   (XX)

In a similar manner, a mixed oligomer (XXI) was obtained.

3'TAGGCCmCmAmCmAmCmAm5'  (XXI)

The mixed oligomers thus obtained were each complementary to the WS-S(+)RNA (XV). The compounds (XVII to XIX) are the mixed oligomers, wherein only the 3'-terminal portion is substituted with the O-methyl RNA. The compounds (XX to XXIII) are the mixed oligomers, wherein only the 5'-terminal portion is substituted with the O-methyl RNA. The compound (XXIV) is the mixed oligomer, wherein both the two terminal portions are individually replaced by the O-methyl RNA, as in the case of the compounds (V—VIII, XI and XII) already mentioned.

The mixed oligomers (XVII to XXIII) are designed for cleavage of phosphodiester bond in the stem region between 19th and 24th segments (counted from the 5'-terminal) in the WS-S(+)RNA. The mixed oligomer (XXIV) is designed for cleavage of phosphodiester in the loop region between 36th and 46th segments.

Table 4 illustrates the complementary arrangement relationship between the mixed oligomers (XVII - XXIV) and the WS-S(+)RNA (XV), and also shows the secondary structure of the WS-S(+)RNA.

With reference to derivatives of the compounds (I–IV) employed for the preparation of the mixed oligomers, it is possible to use, as the radical X, a conventional protecting radical such as trityl, instead of dimethoxy-trityl (-DMTr) or monomethoxy-trityl (-MMTr).

In the method A, the o-chloro-phenyl radical as the phosphate-protecting group may be replaced by an ordinary protecting group, which is customarily used in the synthesis of DNA and RNA, for instance, p-chlorophenyl, cyanoethyl, trichloroethyl or the like. In the method B, it is possible to replace diisopropylamino radical shown as the protecting radical in the formulae $R_2$ and $R_3$, by another protecting group such as dimethylamino, morpholino or the like. Furthermore, the method B may be modified in such a way that an H-phosphonate is used instead of $R_2$ and $R_3$, the acylation is effected with the aid of pivaloyl chloride, and the activation is carried out by using tetrazole. It is also possible to replace the radicals $R_1$, $R_2$ and $R_3$ by methyl phosphonic imidazolide, so as to produce an oligomer, wherein the 5'-hydroxyl radical is connected via a methyl phosphonate group to the 3'-hydroxyl radical.

The methoxy radical as the group Z may be replaced by hydroxyl, alkoxy (which represents a substituted hydroxyl radical having a substituent which cannot be removed by a chemical treatment customarily carried out in the fields of nucleic acid chemistry, for example, ethyl, propyl, butyl or the like), or —OQ, wherein Q represents a protecting radical such as t-butyl-dimethylsilyl or tetrahydropyranyl customarily employed in RNA synthesis.

The cleavage reaction of the low molecular weight RNA (X, XIII, XIV) and the analysis of the cleavage site were carried out in the manner shown below.

The 5'-hydroxyl radical of the RNA molecule (X, XIII, XIV) was labelled with the aid of T4-polynucleotide kinase and [r−$^{32}$P]ATP. Then the RNA was mixed with the complementary DNA oligomer (IX) or the complementary mixed oligomer (V-VIII, XI, XII), and was subjected to a cleavage reaction employing RNaseH. The reaction solution was analysed by homo-chromatography to determine the cleavage position and the degree of cleavage i.e. cleavage rate.

In the reaction step, the $^{32}$P-labelled RNA oligomer (X, XIII, XIV) (30,000 to 40,000 cpm) was mixed with the unlabelled RNA oligomer (X, XIII, XIV) (1–5 μM) and with the DNA oligomer (IX) (10 μM) complementary to the compound (X), or the complementary mixed oligomer (V-VIII, XI, XII) (10-25 μM), in the presence of 40 mM Tris-HCl (pH 7.7), 4 mM MgCl$_2$, 1 mM DTT, 4% glycerol and 0.003% bovine serum albumin. Then an RNase H (5–10 U) derived from E. coli HB101 (Takara Shuzo Co., Ltd.) was added, and the reaction was carried out at 20° C. or 30° C. for 2-48 hours.

The cleavage position was determined according to a method wherein the labelled RNA molecule (X, XIII, XIV) was partially digested with snake venom phosphodiesterase, and the resulting product was analysed by homo-chromatography.

The cleavage position and the cleavage rate were as follows.

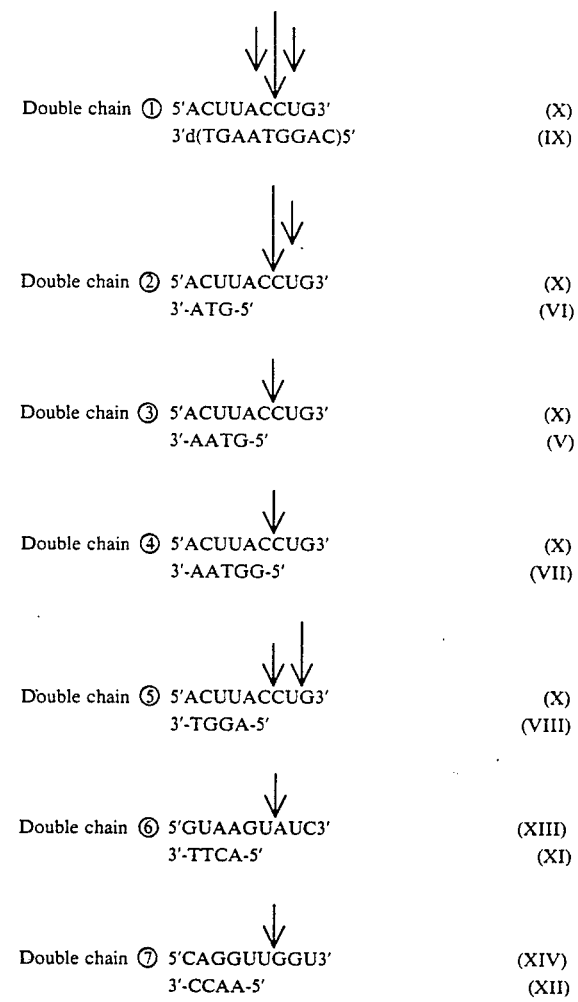

(The line "—" represents a 2'-O-methyl-nucleotide chain, and the arrow mark shows the cleavage position in such a manner that the size of the arrow mark is varied depending on the cleavage rate determined qualitatively.)

In the homo-chromatography, the spots formed were cut out, and the radioactivity thereof was determined in a liquid scintilation counter (PACKARD TRI-CARB 640C) according to the Cherenkou method.

From the above-mentioned experiments, concerning the cleavage of the RNA molecule (X), the following results were obtained. In the case of the double chain with the complementary DNA oligomer (IX), the linkage at the right sides of the 5th, 6th and 7th segments (counted from the 5'-terminal) were cleaved, so that no positional preference was recognized in this reaction. In the case of double chains ③ and ④, wherein the complementary mixed oligomer (V, VII), containing the DNA oligomer consisting of 4 or 5 bases, was present, it was possible to preferentially cleave the linkage at the right side of the 6th segment (counted from the 5'-terminal). When the complementary mixed oligomer (VIII) was employed, the linkage at the right side of the 8th segment (counted from the 5'-terminal) was preferentially cleaved. In the case of the double chains ⑥ and ⑦, wherein the other RNA molecule (XIII, XIV) with the different base sequence, was present, together with the complementary mixed oligomer (XI, XII), it was observed that the linkage at the right side of the 6th segment (counted from the 5'-terminal) was preferentially cleaved, as in the case of the double chain ③.

As explained above, in the case of a low molecular weight RNA (9 mer), it is necessary to use a mixed oligomer having 3 to 6 bases, preferably 4 to 5 bases in length of DNA oligomer. When the mixed oligomer having 4 or 5 in the contiguous length of DNA oligomer in its center part was employed to cleave RNA, cleavage site of RNA by RNaseH can be predicted because the cleavage occurred at the 3'-end on the tetraribonucleotides of, or at the penultimate position on the pentaribonucleotides of the RNA-DNA hybrid regions. In order to enhance the preferential cleavage efficiency, the reaction conditions, including the reaction temperature and the amount of enzyme employed, may be varied in a manner customarily employed in the fields of biochemistry.

In order to examine whether the above-mentioned RNA cleavage method may also apply to a functional RNA having a higher order structure such as second or third order structure, an experiment was carried out wherein an RNA cleavage reaction of the high molecular weight RNA WS-S(+) (XV) was conducted, together with a confirmation operation of the cleavage position. As in the case of the low molecular weight RNA (X), the high molecular weight RNA should be labelled with radioactive phosphorus. Since the WS-S(+)RNA (XV) is prepared by a in vitro transcription, it has a triphosphate component in the 5'-terminal. Therefore, the 3'-terminal was labelled according to a known method (Nature, 275, 560, 1978) with 32 P Cp with the aid of an RNA ligase. The labelled product was subjected to an electrophoresis operation using a 8% polyacrylamide gel which contained 7M urea, and analysed by means of autoradiography. The product was a mixture of a 90 mer and a 91 mer. It is not clear why the product was obtained as the mixture. The mixture was separated by the same gel-electrophoresis, and extracted from the gel in a conventional manner, so that the WS-S(+)RNA, having the 3'-terminal labelled, was obtained. The labelled RNA was dissolved in water in a concentration of 0.02 pmole/μl, and used in the following experiment.

The WS-S(+)RNA having the labelled 3'-terminal (3.3 nM) was mixed with 40 mM Tris-HCl (pH 7.7), 4 mM MgCl$_2$, 0.003% BSA, 1 mM DTT, 4% glycerol, the mixed oligomer (83-8.3 μl) and RNaseH (0.17-0.83 unit/μl), and a reaction operation was effected for several hours, with the proviso that, before the RNaseH was added, the mixture was heated to 65° C. for 2 minutes to effect annealing. The reaction was carried out at 30° C., and then the reaction mixture was admixed with a loading sol. (which contained 10 M urea, 0.02% xylene cyanol and 0.02% bromophenol blue) to stop the reaction. The product was subjected to an electrophoresis operation using 8% polyacrylamide gel which contained 7 M urea, and then analysed by autoradiography to determine the cleavage position. As the size marker, the samples which were prepared by an alkaline hydrolysis, RNaseT$_1$, RNaseU$_2$, RNase PhyM digestions of the WS-S(+)RNA having the labelled 3'-terminal, were used.

The result of this experiment, concerning the cleavage reaction, is shown in Table 5 wherein the cleavage position is indicated by an arrow.

The cleavage efficiency of the mixed oligomer, having the DNA moiety in the 5'-side, was higher than that of the mixed oligomer having the DNA moiety in the 3'-side. As the reason for this, it is considered that in the former case, there is a complementary adaptability in the area including the strands of the both sides of the stem structure $A^7$ to $U^{24}$, whereas, in the latter case, there is a complementary adaptability only in strands $C^{19}$ to $U^{24}$ in the stem, and that such a difference in complementary adaptability gives an influence on the formation of a stable complementary double chain which is important for the cleavage reaction. Only with the above consideration, it is not fully understood the difference of the cleavage reaction efficiency due to whether the DNA moiety is present in the 5'-terminal. It is a matter for deep reflection that the secondary structure of DNA has an influence on the cleavage reaction. For instance, it was observed that the cleavage occurred more rapidly in the mixed oligomer (XXIV) having a complementary portion in the loop, as compared with the other oligomers.

In the case of the compounds (XVII, XVIII, XIX) having the DNA moiety in the 5'-side, these compounds have the same complementary area, but they are different in the length of the DNA moiety, and also somewhat different in the cleavage position. In all of the above-mentioned experiments, in the case of the compound (XVIII), the cleavage occurred only at the position between $G^{21}$ and $G^{22}$ of WS-S(+)RNA. In the case of the compound (XIX), wherein the length of the DNA moiety was shorter by 1 base than that of the DNA moiety contained in the compound (XVIII), the cleavage occurred in the position between $G^{21}$ and $G^2$ of WS-S(+)RNA, and also in the other position which was nearer by 1 base towards the 5'-side (on the mixed oligomer) than the former position between $G^{21}$ and $G^{22}$. In the case of the compound (XVII), wherein the length of the DNA moiety is longer by 1 base towards the 3'-side, the cleavage occurred preferentially in the position which was nearer by 1 base than the cleavage position using the compound (XVIII). Therefore, it may be said that, when a mixed oligomer, wherein a 2'-O-methyl RNA is present in the 3'-side and a DNA moiety is present in the 5'-side, is used, then the cleavage will preferentially occur in the position corresponding to between the 4th and the 5th segments counted from the 3'-side of the DNA moiety. This conclusion is based on the result of the experiment wherein use was made of the mixed oligomers having an O-methyl RNA only in one side, which was not used in the cleavage reaction of the low molecular weight RNA (X, XIII, XIV). The result mentioned above coincides with that obtained in the experiment of the cleavage reaction of the low molecular weight RNA (X).

On the other hand, when the mixed oligomers (XX, XXI), wherein the 2'-O-methyl RNA is present in the 5'-side and the DNA moiety is present in the 3'-side, were used, then the following results were obtained. In the case of the compound (XXI), the cleavage occurred in one position with a low cleavage efficiency under the influence of the second order structure of WS-S(+) (XV). In the case of the oligomer (XXIV) having the O-methyl RNA in both sides, the cleavage occurred in the position which was nearer by 1 base towards the 3'-side on the RNA molecule than the cleavage position of the low molecular weight RNA (X, XIII, XIV). Thus, the cleavage position of RNA molecule in the case of the mixed oligomer (XXIV) was different by 1 base from the cleavage position of the low molecular weight RNA (X, XIII, XIV).

Figures 1, 10:
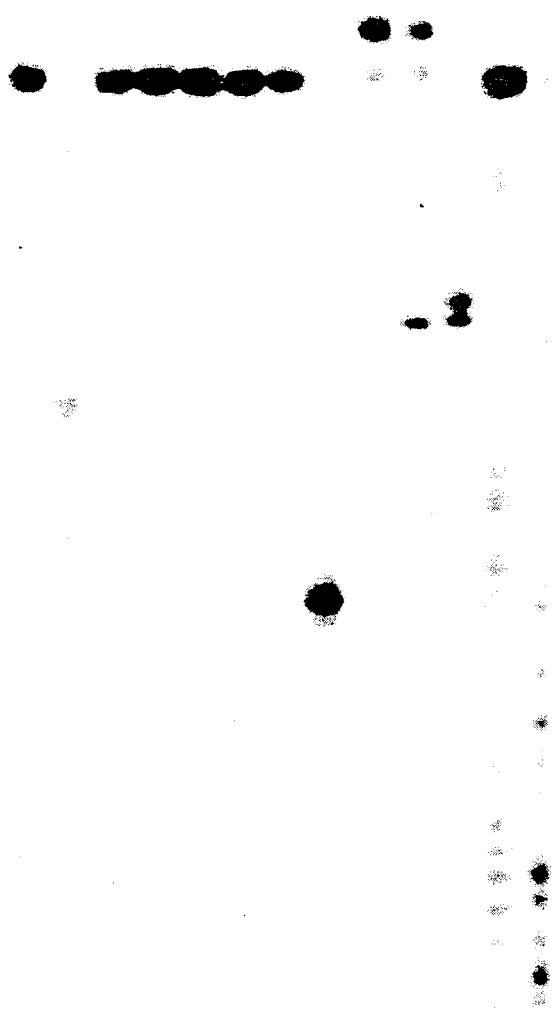
Figures 2, 10:
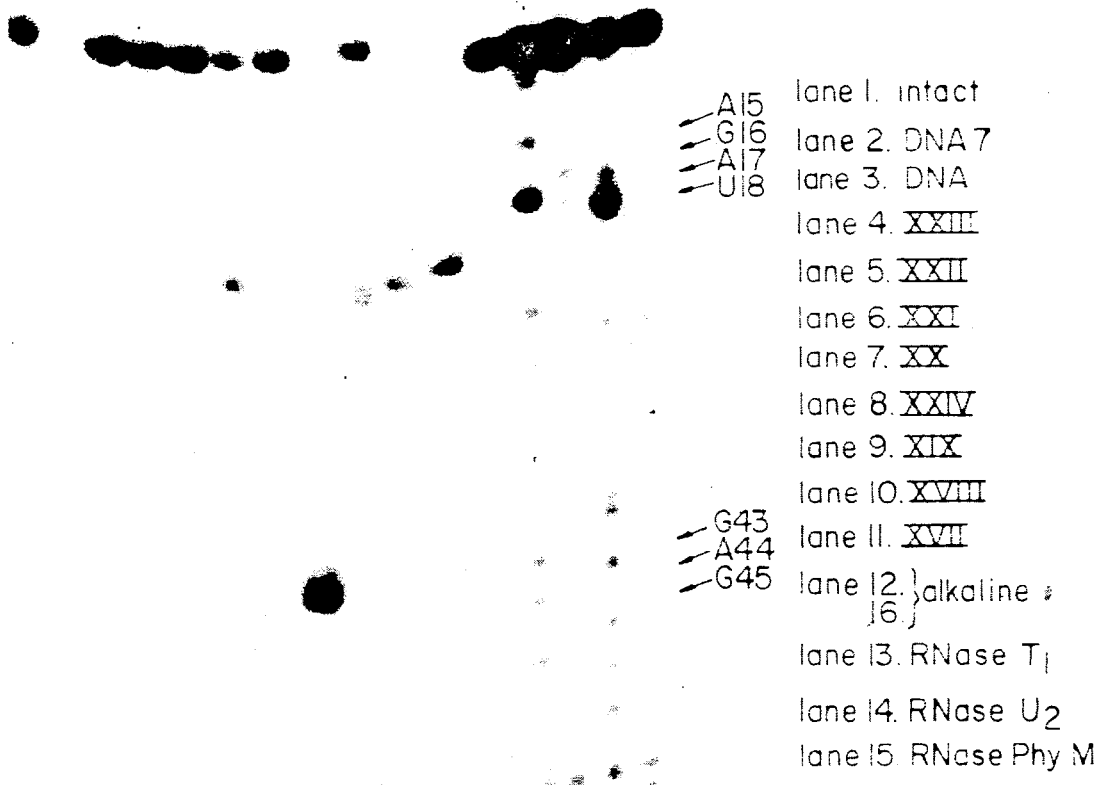

The cleavage position was determined according to a method wherein the 5'-terminal of the cleaved fragment is labelled with $^{32}P$, followed by nuclease $P_1$ digestion to obtain the 5'terminal-nucleotide unit, which is then analysed by a filter paper electrophoresis (see Example 23). In the case of the compound (XXI), the cleavage position was determined on the basis of the electrophoresis data of the fragments of the cleaved oligomer as shown in FIG. 10-2.

As is apparent from the above, the method for design and preparing the mixed oligomers mentioned above may apply to the case where a low molecular weight RNA is to be cleaved with the proviso that the RNA is not in the state of second order structure.

Furthermore, the above-mentioned method for design and preparing the mixed oligomers may apply even to the cleavage of a high molecular RNA, in consideration of the following matters. Namely, it is necessary to design a mixed oligomer in consideration of the aimed cleavage position which may be in the loop, or in the stem, and also in consideration of the second order structure. In addition, it is necessary to determine which is more suitable, a mixed oligomer having O-methyl RNA in the 3'-side, or another mixed oligomer having such RNA in the 5'-side.

The number of the DNA oligomers contained in the mixed oligomer is generally between 3 and 6, preferably between 4 and 5.

In order to increase the positional selectivity of the cleavage reaction, the reaction conditions such as the reaction temperature and the amount of enzyme used may be varied in a manner customarily employed in the fields of biochemistry.

Thus, the invention provides a novel method for the specific cleavage of an RNA molecule, having a wide applicability.

Next, the present invention will be illustrated in more detail by way of the Examples.

EXAMPLE 1

Preparation of a mixed oligonucleotide,

 (V)

wherein m represents an O-methyl-nucleotide unit, and other symbols each represent a deoxynucleotide unit.

A reaction vessel with a glass filter was charged with 50 mg of a polystyrene resin containing 1% of crosslinkages and combined with 6 μmoles of 5'-O-dimethoxytrityl-2'-O-methyl-uridine. This material was washed three times with 2 ml of a dichloromethane/methanol mixture (volume ratio of 7:3).

Next, 2 ml of a 2% solution of benzenesulfonic acid in a dichloromethane/methanol mixture (volume ratio of 7:3) were added, and the reaction mixture was shaken for 1 minute. After the reaction, the reaction solution was filtered, and the resin was washed with 2 ml of a dichloromethane/methanol mixture (volume ratio of 7:3). A further reaction was conducted with the aid of further 2 ml of 2% benzenesulfonic acid solution for 1 minute. The reaction solution was washed two times with 2 ml of the above-mentioned washing mixture, and then washed three times with 2 ml of pyridine. Then the reaction mixture was admixed with 0.3 ml of pyridine, and the resin was dried by distilling off the pyridine under reduced pressure.

Thereafter, to the reaction system a solution of 5'-dimethoxytrityl-2'-O-methylguanine-3'-o-chlorophenyl-phosphoric acid (IIIb1) in pyridine (20 mg/0.3 ml) was added, and the pyridine was distilled off under reduced pressure. A solution of mesitylenesulfonyl-3-nitrotriazole in pyridine (20 mg/0.3 ml) was added, and the reaction mixture was heated to a temperature of 40° C., and shaken for 20 minutes. The reaction solution was separated from the resin by means of filtration, and the resin was washed two times with 2 ml of pyridine.

Next, to the reaction system 1.8 ml of a 0.1 M dimethylaminopyridine solution and 0.2 ml of acetic anhydride were added, and the reaction mixture was shaken for 3 minutes, so that the unreacted 5'-hydroxyl group was capped with an acetyl group. After the reaction solution had been filtered off, the resin was washed three times with 2 ml of pyridine.

By repeating the operation mentioned above, the nucleotide units $IId_1$, $IId_1$, $IVd_1$, $IIId_1$, $IIIb_1$, $IIb_1$ and $Ib_1$ were successively coupled with the previously formed unit in this order to extend the chain length. The yield of each coupling reaction was 47 to 105%. The yield was determined by a method wherein the dimethoxytritanole formed by the de-dimethoxy tritylation was treated with a perchloric acid-ethanol mixture to form a colored product, and the light absorption of the colored product at 500 nm was measured. The overall yield was 25%.

After the completion of the above-mentioned reactions, the resin was washed with dioxane, and admixed with 0.5 ml of a 1 M solution of 2-pyridinylaldoximetetramethylguanidine in dioxane, 0.4 ml of dioxane and 0.1 ml of water, and the reaction mixture was shaken at 30° C. overnight. The solution was separated from the resin by filtration. The resin was washed three times with 2 ml of 50% aqueous pyridine solution. The filtrate and the washing solution were combined, and the resulting mixture was evaporated to remove the solvent. The residue was dissolved in 1 ml of pyridine and placed in a closed tube. After 10 ml of a 28% ammonia water had been added, the tube was sealed and a reaction operation was conducted at 60° C. for 5 hours.

The reaction solution was concentrated under a reduced pressure to dryness, and was subjected to column chromatography employing a column having a diameter of 0.7 cm and a length of 12 cm, and a reversed phase silica gel ("Bondapack C 18" produced by Waters Co., Ltd.; particle size: 35 to 100 μ). As the mobile phase, a 50 mM acetic acid-triethylamine buffer solution with a linear concentration gradient from 5 to 35% of acetonitrile was used. The quantitative determination was effected on the basis of the light absorption at 254 nm. By this chromatography, a 5'-dimethoxy-trityl-mixed oligo-nucleotide was separated. After the solvent had been evaporated under reduced pressure, 1 ml of a 80% aqueous acetic acid solution was added, and the reaction solution was kept at room temperature for 20 minutes. The reaction solution was evaporated under reduced pressure, and then co-evaporated with water to remove the acetic acid.

The residue was dissolved in water, washed with ethyl acetate, and the aqueous phase was evaporated under reduced pressure, and purified by a high performance liquid chromatography using "Nucleosil C18". As the mobile phase, a 0.1 M acetic acid/triethylamine buffer solution (pH 7.0) with a linear concentration of 13 to 21% was used at a flow rate of 1 ml/minute. A main peak (i.e. main fraction) of eluant was recovered so that 0.07 μmole of a mixed oligo-nucleotide was obtained in a yield of 1.17%.

The mixed oligo-nucleotide thus formed was analysed by a high performance liquid chromatography with an anion exchange column "DEAE2SW". In this analysis, a single peak was observed, so that it was confirmed that the product was pure.

An operation for the confirmation of the nucleotide sequence in the mixed oligo-nucleotide was conducted according to a method disclosed in Proc. Natl. Acad. Sci., U.S.A., 70, 1209–1213, 1973, with the proviso that 0.050 D unit of the oligo-nucleotide was used, and the terminal 5'-hydroxy radical was phosphorylated with the aid of a labelling element, $^{32}P$. By autoradiography, it was confirmed that the above-mentioned base sequence was correct.

Also, other mixed oligo-nucleotides (VI–VIII, XI, XII) were prepared in a manner similar to that shown above.

EXAMPLE 2

Reactions for cleavage of the double chain

A labelled RNA oligomer (X, 20,000 cpm), an unlabelled RNA oligomer (X, 1 μM) and a complementary DNA oligomer (IX, 10 μM) prepared by a method according to Ikehara et al (Publication 2), were separately admixed with 40 mM of Tris-HCl (pH 7.7), 4 mM of $MgCl_2$, 1 mM of DTT, 4% of glycerol, 0.003% of BSA (Cooper Biochemical Inc., Worthington Biochemicals, Nuclase free) and RNaseH (5 U). The resulting mixture (20 μl in total) was subjected to a reaction operation at 20° C. 4 μl of the sample was periodically taken out, and analysed by means of a homochromatography (FIG. 1).

Next, each spot was separated out, and the radioactivity thereof was measured by a scintillation counter, and the cleavage rate was calculated (FIG. 2). FIG. 3 shows a graph illustrating the relationship between the cleavage position and the cleavage rate.

In view of the results thus obtained, it is concluded that the cleavage of the chemical chain occurred at the plural position at different degree as shown below by arrows. Namely, the cleavage occurred in the phosphodiester bond between the 5th and the 6th segments, the bond between the 6th and the 7th segments, and the bonds between the 7th and 8th segments (counted from the 5'-terminal) in the RNA oligomer (X).

| Double chain ① | 5'ACUUACCUG3' | (X) |
| | 3'd(TGAATGGAC)5' | (IX) |

In the above formula, the arrows indicate the cleaved positions, and the size of the arrows qualitatively shows the degree of the cleavage reaction.

EXAMPLE 3

Reactions for cleavage of the double chains ② and ④

A labelled RNA oligomer (X, 40,000 cpm), an unlabelled RNA oligomer (X, 5 μM) and a complementary mixed oligomer (VI or VII, 25 μM) were admixed with the buffer solution as in Example 2, and RNaseH (5 U) was added. The resulting mixture each (10 μl) were subjected to a reaction operation at 20° C. for 48 hours (FIG. 4) or at 30° C. for 16 hours (FIG. 5). The reaction products were analysed as in the case of Example 2.

Results

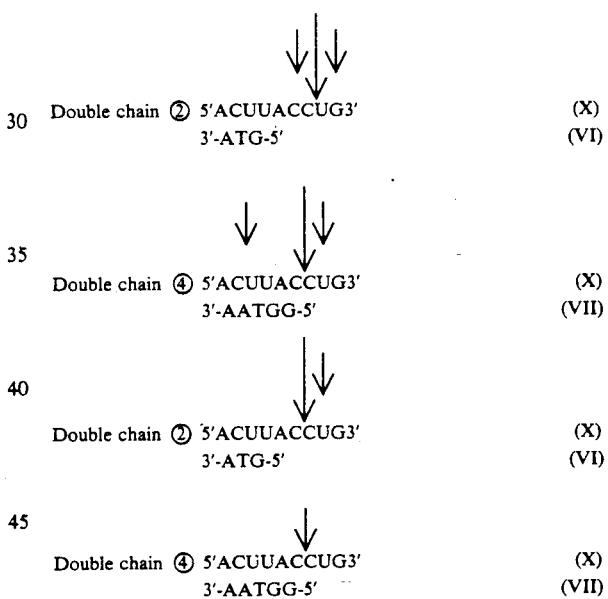

wherein the line "—" represents an O-methyl oligomer portion.

As shown above, it has been possible to preferentially cleave the chemical bond between the 6th and the 7th segments (counted from the 5'-terminal) in the RNA oligomer (X), if the reaction operation was carried out using the mixed oligomer (VII) at 30° C. for 16 hours.

EXAMPLE 4

Reactions for cleavage of the double chain ③

A labelled RNA oligomer (X, 30,000 cpm), an unlabelled RNA oligomer (X, 1 μM) and a complementary mixed oligomer (V, 10 μM) were separately admixed in the same buffer solution as in Example 2, and RNaseH (10 U) was added.

Figure 6:
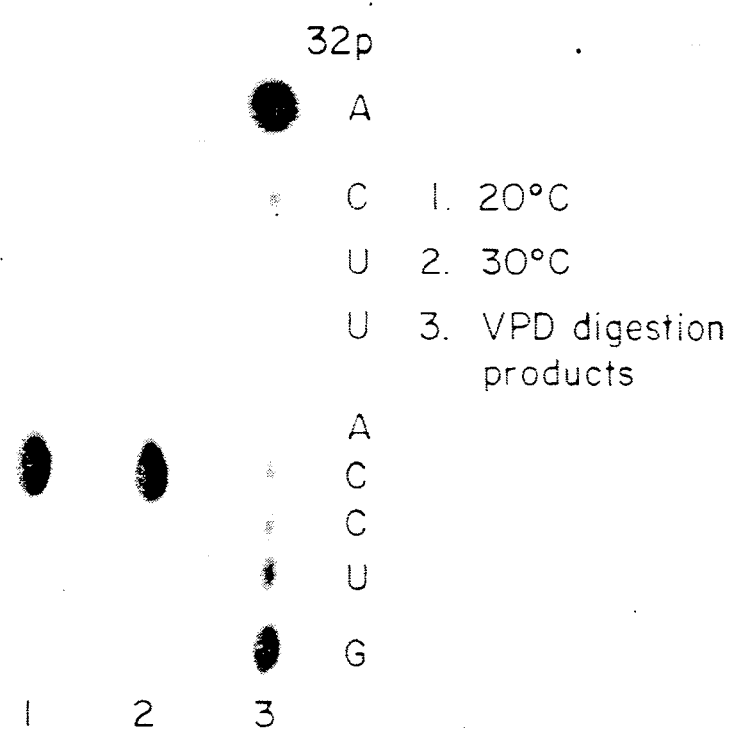

Each of the mixtures (20 μl) thus obtained was subjected to a reaction operation at 20° C. or 30° C. for 17 hours, and thereafter each reaction product was analysed as in the case of Example 2 (FIG. 6).

Results:

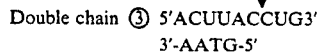

Double chain ③ 5'ACUUACCUG3'     (X)
                3'-AATG-5'        (V)

As shown above, it has been possible to preferentially cleave the chemical bond between the 6th and 7th segments (counted from the 5'-terminal) in the RNA oligomer (X) by using the mixed oligomer (V).

EXAMPLE 5

Reactions for cleavage of the double chain ⑤

Figure 7:
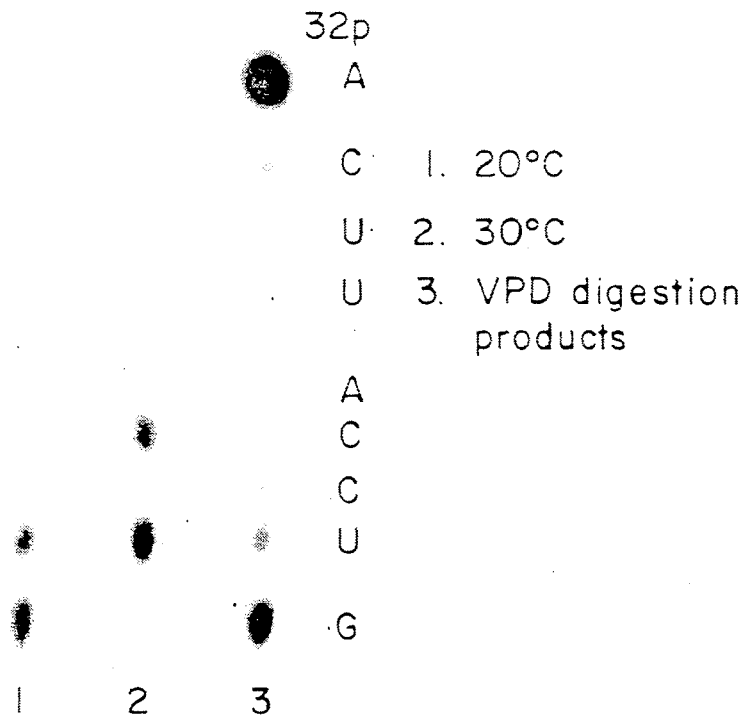

A labelled RNA oligomer (X, 30,000 cpm), an unlabelled RNA oligomer (X, 1 μM) and a complementary mixed oligomer (VIII, 10 μM) were separately mixed with the same buffer solution as in Example 2, and RNaseH (10 U) was added. The amount of each starting mixture was 20 μl. Each mixture was subjected to a reaction operation at 20° C. or 30° C. for 17 hours, and thereafter the products each were analysed as in Example 2 (FIG. 7).
Results:

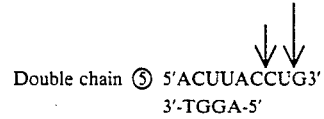

Double chain ⑤ 5'ACUUACCUG3'     (X)
                3'-TGGA-5'        (VIII)

As shown above, it has been possible to preferentially cleave the chemical bond between the 8th and 9th segments (counted from the 5'-terminal) in the RNA oligomer (X) by using the mixed oligomer (VIII).

EXAMPLE 6

Reactions for cleavage of the double chain ⑥

Figure 8:
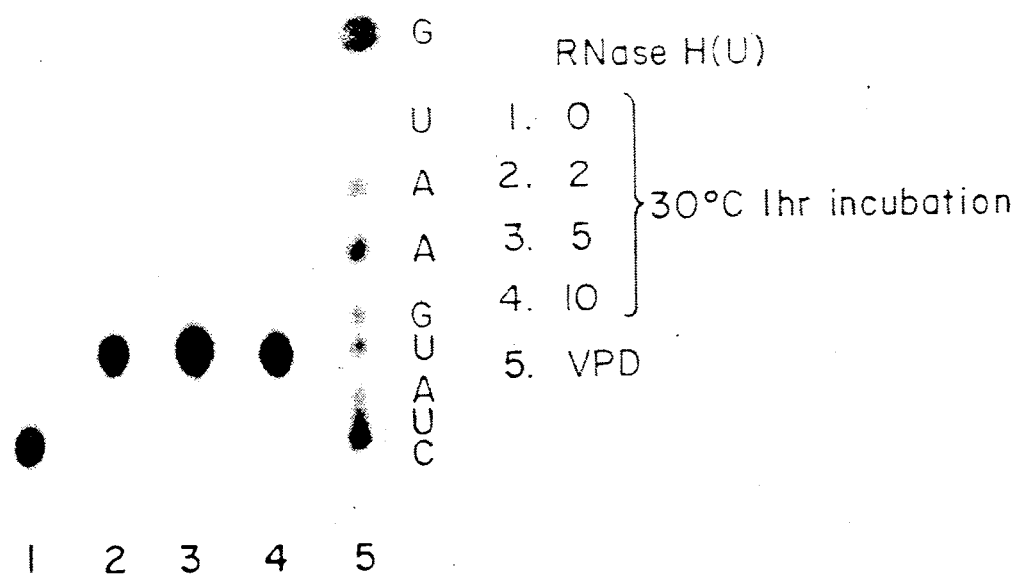

A labelled RNA oligomer (XIII, 30,000cpm), an unlabelled RNA oligomer (XIII, 1 μM) and a complementary mixed oligomer (XI, 10 μM) were separately mixed with the same buffer solution as in Example 2, and RNaseH (0, 2, 5 or 10 U) was added. The amount of each starting mixture was 20 μl. These mixtures each were subjected to a reaction at 30° C. for 1 hour, and the reaction products were analysed as in the case of Example 2 (FIG. 8).
Results:

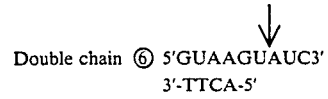

Double chain ⑥ 5'GUAAGUAUC3'     (XIII)
                3'-TTCA-5'        (XI)

As shown above, it has been possible to preferentially cleave the chemical bond between the 6th and 7th segments (counted from the 5'-terminal) in the RNA oligomer (XIII).

EXAMPLE 7

Reactions for cleavage of the double chain ⑦

Figure 9:
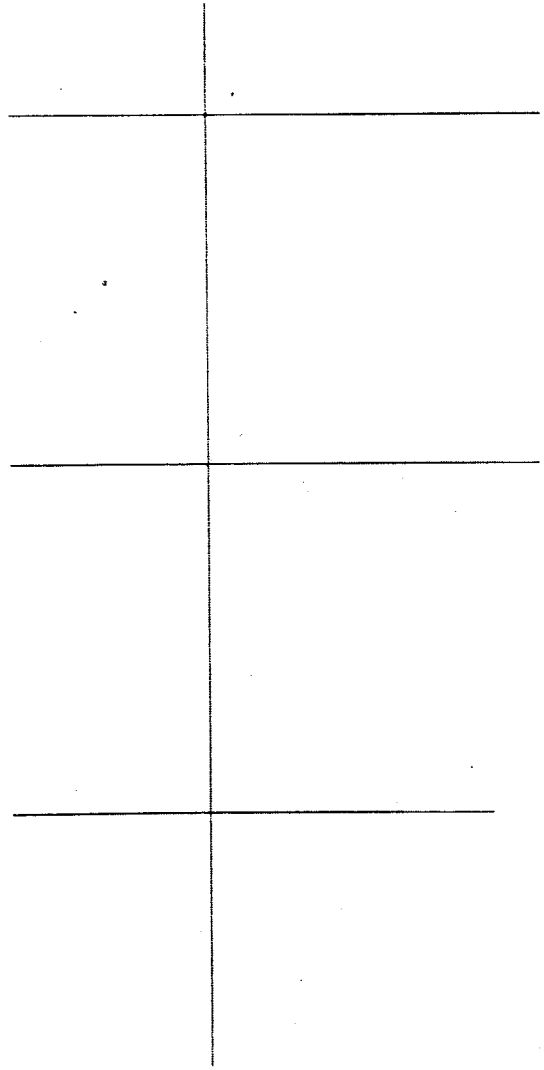

A labelled RNA (XIV, 30,000 cpm), an unlabelled RNA (XIV, 1 μM) and a complementary mixed oligomer (XII, 10 μM) were separately mixed with the same buffer solution as in Example 2, and RNaseH (5 U) was added. The amount of each starting mixture was 20 μl. These starting mixtures each were subjected to a reaction at 20° C. for 30 minutes or 12 hours, or at 30° C. for 30 minutes or 12 hours. The reaction products thus obtained were analysed as in the case of Example 2 (FIG. 9).
Results:

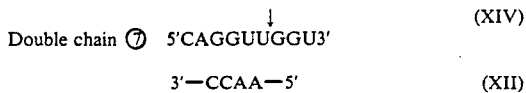

Double chain ⑦ 5'CAGGUUGGU3'     (XIV)
                3'—CCAA—5'       (XII)

As shown above, it has been possible to preferentially cleave the chemical bond between the 6th and the 7th segments (counted from the 5'-terminal) in the RNA oligomer (XIV).

EXAMPLE 8

Method for the labelling of 5'-hydroxyl group of RNA oligomers (X, XIII and XIV) with a phosphate containing $^{32}$P.

20 pmde of RNA oligomer (X) [prepared according to the method by Iwai et al; publication (3)], and 30 μCi of [r-32P] ATP (3,000 Ci/mmole, NEN), 50 mM of Tris-HCl (pH 8.0), 10 mM of MgCl$_2$, 'mM of EDTA, 6 mM of DTT and 0.1 mg/ml of gelatin were mixed with one another to form 25 μl of a mixture. The mixture was admixed with T4-polynucleotide Kinase (1 U; prepared by Takara Brewery Co., Ltd.), and subjected to a reaction operation at 37° C. for 1 hour to effect the phosphorylation of the 5'-terminal group.

After this reaction, the reaction mixture was extracted by a phenol-chloroform mixture. Then a chromatographic operation was conducted in the Sefadex-G-75-column (total volume of 10 ml). As the mobile phase, use was made of 10 mM of triethylamine-bicarbonate buffer solution (pH 7.0). The initial radioactive fractions were collected and used a the labelled RNA oligomers.

As for the RNA oligomers (XIII, XIV), a similar operation was conducted to prepare the labelled RNA oligomer samples.

EXAMPLE 9

Homo-chromatography

A suitable amount (of the order of $10^4$ cpm) of an enzyme reaction solution was spotted on "Polygram Cel 300 DEAE/HR-2/15" (Mecherey-Nagel Company), and developed with Homomix-VI at 60° C. Thereafter, exposure of an X-ray film ("Kodak-X-Phomat-RP-Film" supplied by Eastman Kodak Company) to this sample was carried out overnight at −80° C.

The Homomix employed here was one which had been prepared according to a method described in the article by E. Jay et al ("Nucleic Acids Res.", 1, 331, 1974).

EXAMPLE 10

Partial digestion by Venom phospho-diesterase (Preparation of VPD digestion products)

An RNA oligomer labelled at its 5'-terminal (X, XIII, XIV; 5 to 7×10$^4$ cpm) was mixed with 0.2 to 0.3 OD of a carrier RNA (Tolura yeast RNA Type VI, supplied by SIGMA Company), 0.25 M of Tris-HCl (pH 8.0), 50 mM of MgCl$_2$ and 0.2 to 0.3 μg of VPDase (Boehringer Company) to form 10 μl of a mixture. This mixture was subjected to a reaction operation at 37° C. During the reaction, a sample (2 μl) of the reaction mixture was taken out 2 minutes after the beginning of the reaction. The sample was added to 5 μl of 5 mM EDTA in an eppen tube, and heated at 100° C. for 2 minutes to stop the reaction of the sample. Such sampling operations were also conducted 5, 10, 20 and 30 minutes after the beginning of the reaction operation. These reaction mixtures were mixed and used as markers in the homochromatography. (They are shown as "VPD digestion products" in FIGS. 1, 4, 5, 6, 7, 8 and 9).

EXAMPLE 11

Preparation of 2'-O-methyl-nucleoside-3'-phosphoroamidites ($Ib_2$, $IIb_2$, $IIIb_2$, $IVb_2$)

344 mg (0.5 mmole) of $N^6$-benzoyl-5'-O-dimethoxytrityl-2'-O-methyl-adenosine (compound IIa) were dissolved in 2 ml of anhydrous THF, and the resulting solution was admixed with 362 μl (2 mmoles) of diisopropyl ethyl amine (DIPEA) with stirring under an argon atmosphere at room temperature. Then 300 μl (1.5 mmoles) of N,N-diisopropyl-amino-methoxychlorophosphine was added over 1 minute. After 5 minutes, DIPEA hydrochloride was formed as a white precipitate. Stirring was continued at room temperature and, after 45 minutes, the reaction mixture was analysed by a chromatography using silica gel 60 TLC (the mobile phase: n-hexane/acetone (1:1) containing 5% of triethyl amine) to confirm whether the spot of the starting material ($R_f=0.52$) had disappeared and the spot of the product ($IIb_2$) ($R_f=0.76$) had appeared. After the confirmation of the latter spot, 20 ml of ethyl acetate was added to the reaction mixture under cooling with ice. Then the reaction mixture was washed twice with 15 ml of an ice-cooled saturated aqueous sodium bicarbonate solution, and then washed once with 15 ml of an ice-cooled saturated aqueous sodium chloride solution. The organic phase was dried over anhydrous sodium sulfate. After the sodium sulfate had been separated by a filtration, the filtrate was evaporated to dryness. The oily residue thus obtained was dried under reduced pressure, and dissolved in 2 ml of dichloromethane, and added dropwise with stirring to 200 ml of n-hexane which had been cooled to a temperature of −50° C., whereby a white precipitate was formed The white precipitate was filtered, and immediately placed in a desiccator to dry it under a reduced pressure overnight. 407 mg of the product ($IIb_2$) were obtained in a yield of 95%.

In a similar manner, the following products were obtained in a similar yield: $N^2$-isobutyryl-5'-O-monomethoxytrityl- 2'-O-methyl-guanosine-3'-phosphoroamidite ($IIIB_2$), $N^4$-benzoyl-5'-O-dimethoxytrityl-2'-O-methyl-cytidine-3'-phosphoroamidite ($Ib_2$), and 5'-O-dimethoxytrityl-2'-O-methyl-uridine-3'-O-phosphoroamidite ($IVb_2$).

The spectral data of these products, including $^{31}P$-NMR-spectra, FAB-Mass spectra and UV-absorption spectra, are shown below.

P-NMR spectra:
Solvent: $CDCl_3$; External standard: trimethyl phosphate
(PPM)

| | |
|---|---|
| $Ib_2$ | 148.5470, 148.3509 |
| $IIb_2$ | 149.4520, 148.5998 |
| $IIIb_2$ | 149.5726, 148.9618 |
| $IVb_2$ | 148.8788, 148.3132 |

(These data show two signals due to the isomers.)
FAB-Mass spectra:

| | $M-H^+$ (m/z) |
|---|---|
| $Ib_2$ | 825 |
| $IIb_2$ | 849 |
| $IIIb_2$ | 801 |
| $IVb_2$ | 722 |

UV-absorption spectra:
Solvent: ethanol

| | (nm) |
|---|---|
| $Ib_2$ | $\lambda_{max.}$ 305, 261, 236 |
| | $\lambda_{min.}$ 290, 249, 224 |
| $IIb_2$ | $\lambda_{max.}$ 280, 234 |
| | $\lambda_{min.}$ 257, 224 |
| $IIIb_2$ | $\lambda_{max.}$ 282, 254, 236 |
| | $\lambda_{min.}$ 273, 244, 227 |
| $IVb_2$ | $\lambda_{max.}$ 265, 225 |
| | $\lambda_{min.}$ 254, 226 |

EXAMPLE 12

Preparation of 2'-O-methyl-nucleoside-3'-β-cyanoethyl-N,N-diisopropyl-aminophosphines ($Ib_3$, $IIb_3$, $IIIb_3$, $IVb_3$)

344 mg (0.5 mmole) of $N^6$-benzoyl-5'-O-dimethoxytrityl-2'-O-methyladenosine were dissolved in 2 ml of THF (which had been distilled in the presence of metallic sodium). To the resultant mixture, 362 μl (2 mmoles) of diisopropyl ethyl amine (DIPEA) was added. Thereafter, 1.5 mmoles of N,N-diisopropylamino-8-cyanoethylchlorophosphine were added. After 5 minutes, a white precipitate of DIPEA hydrochloride was formed, and the stirring was further continued. After 30 minutes, a portion of the reaction mixture was analysed by chromatography employing silica gel 60 TLC (the mobile phase: n-hexane/acetone (1:1) containing 5% of triethyl amine) in order to confirm whether the spot of the starting compound IIa had disappeared and the spot of the amidite ($IIb_3$) had appeared. After that, 20 ml of ethyl acetate was added to the reaction mixture under cooling with ice. Then the reaction mixture was washed with twice with 15 ml of a saturated aqueous sodium bicarbonate solution, and with 15 ml of an ice-cooled saturated aqueous sodium chloride solution. The organic phase was dried over sodium sulfate.

After the sodium sulfate had been removed by filtration, the filtrate was evaporated to dryness, the resulting foamy residue was dissolved in 2 ml of ethyl acetate which contained 0.2% of trimethyl amine. The solution thus obtained was subjected to chromatography using a column filled with 2.5 g of silica gel 60. The mobile phase was ethyl acetate containing 0.2% of triethyl amine. The fractions, consisting of pure compound ($IIb_3$), were collected and concentrated to dryness. 407 mg (0.485 mmole) of the compound ($IIb_3$) were obtained in a yield of 97%.

In a similar manner, the following compounds were obtained in almost similar yields: $N^2$-isobutyryl-5'-O-monomethoxytrityl-2'-O-methylguanosine-3'-phosphoramidite (compound $IIIb_3$), $N^4$-benzoyl-5'-O-dimethoxytrityl-2'-O-methylcytidine-3'-phosphoramidite (compound $Ib_3$), and 5'-O-dimethoxytrityl-2'-O-methyluridine-3'-phosphoramidite (compound $IVb_3$).

The spectral data of these compounds, including $^{31}P$-NMR-spectra, FAB-mass spectra and UV-absorption spectra, are shown below.

P-NMR-spectra:
Solvent: CDCl₃; External standard: trimethyl phosphate (8 ppm)

| | (ppm) |
|---|---|
| Compound Ib₃ | 148, 8127, 148, 3224 |
| Compound IIb₃ | 149, 2125, 148, 4582 |
| Compound IIIb₃ | 148, 4582, 148, 2545 |
| Compound IVb₃ | 148, 8203, 148, 3601 |

FAB-Mass Spectra:

| | M·H⁺ (m/z) |
|---|---|
| Compound Ib₃ | 864 |
| Compound IIb₃ | 888 |
| Compound IIIb₃ | 840 |
| Compound IVb₃ | 762 |

UV-absorption spectra:
Solvent: ethanol

| | (nm) |
|---|---|
| Compound Ib₃ | $\lambda_{max}$. 305, 260, 236 |
| | $\lambda_{min}$. 289, 250, 223 |
| Compound IIb₃ | $\lambda_{max}$. 279, 234 |
| | $\lambda_{min}$. 257, 223 |
| Compound IIIb₃ | $\lambda_{max}$. 280, 254, 235 |
| | $\lambda_{min}$. 272, 244, 227 |
| Compound IVb₃ | $\lambda_{max}$. 264, 233 |
| | $\lambda_{min}$. 253, 226 |

EXAMPLE 13

Preparation of 2'-O-methylnucleoside-polymer support (Ic₂, IIc₂, IIIc₂, IVc₂)

344 mg (0.5 mmole) of $N^6$-benzoyl-5'-O-dimethoxytrityl-2'-O-methyladenosine (IIa) and 92 mg (0.75 mmole) of 4-N,N-dimethylamino-pyridine (DMAP) were dissolved in 2 ml of anhydrous pyridine. The resulting solution was admixed with 750 mg (0.75 mmole) of succinic anhydride with stirring at 30° C. The reaction mixture was further stirred overnight, and then evaporated to dryness. The oily residue thus obtained was dissolved in 20 ml of chloroform, and the resulting solution was washed three times with 20 ml of a 0.1 M triethyl ammonium bicarbonate buffer solution (TEAB-buffer solution) (pH 7.5). The chloroform phase was dried over anhydrous sodium sulfate, and evaporated to dryness. The residue thus obtained (a mixture of IIe and DMAP) was dissolved in 2.7 ml of DMF, and the resulting solution was admixed with 200 mg (0.75 mmole) of pentachlorophenol and 154 mg (0.75 mmole) of dicyclohexyl-carbodiimide (DCC), and stirred overnight at 30° C.

The insoluble matter thus formed was removed from the reaction mixture by filtration, and the filtrate was concentrated to dryness The resulting residue was dissolved in 3 ml of chloroform The solution thus formed was subjected to chromatography using a column filled with silica gel 60 (20 g, column size: 4 cm (diameter) × 2.5 cm (length)) which had been equilibrated with chloroform. As the mobile phase, chloroform was used. The eluted fractions, consisting of the compound (IIf) ($R_f$=0.81, measured under such a condition that chloroform: methanol = 20:1 in the silica gel 60 TLC) were collected, and evaporated to dryness The compound (IIf) was obtained in a yield of about 90%.

In a similar manner, the compounds (If, IIIf, IVf) were obtained in almost similar yields.

| Compound | Rf (in silica gel 60 TLC) | Mobile phase |
|---|---|---|
| | Rf | |
| If | 0.76 | chloroform:methanol = 15:1 |

-continued

| Compound | Rf (in silica gel 60 TLC) | Mobile phase |
|---|---|---|
| | Rf | |
| IIIf | 0.68 | chloroform:methanol = 10:1 |
| IVf | 0.74 | chloroform:methanol = 15:1 |

A reaction vessel, provided with a glass filter, was charged with 680 mg of a controlled pore glass support (CPG/long chain alkylamine, pore diameter 500 Å, particle size: 122-177 μ, NH₂-: 30 μmoles/g, Pierce Chemical Co.), washed with 1 ml of DMF, and dried in an argon atmosphere for 1 minute.

Each of the active esters (If, IIf, IIIf, IVf) (0.45 mmole) was dissolved in 4.5 ml of DMF, and 114 μl (0.82 mmole) of triethylamine was added. The resulting solution was added to the above-mentioned CPG, and the vessel was tightly sealed, and shaken overnight at 30° C.

Thereafter, the reaction mixture was filtered under an argon gas pressure The polymer support was washed three times with 5 ml of DMF, and then three times with 5 ml of THF, and dried by an argon gas current for 1 minute.

To the polymer support a liquid mixture consisting of 273 mg of DMAP, 940 mg of 2,6-lutidine, 0.44 ml of acetic anhydride and 4 ml of THF was added. The resultant mixture was shaken at 30° C for 30 minutes to protect the unreacted amino groups. The reaction solution was filtered, washed three times with 5 ml of THF and three times with 5 ml of diethyl ether, and dried in an argon stream and then in vacuum.

A small portion of each nucleotide-support thus obtained (Ic₂, IIc₂, IIIc₂, IVc₂) was treated with 3% trichloro-acetic acid to remove the dimethoxy-trityl groups (or the monomethoxy-trityl group) therefrom, so that free tritanol was formed. The tritanol was subjected to colorimetric quantitative analysis with the aid of a perchloric acid-ethanol solution. It was observed in each case that the amount of the nucleoside bound was 29-30 μmoles/g.

EXAMPLE 14

Preparation of a mixed oligo-nucleotide of the formula

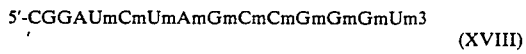

5'-CGGAUmCmUmAmGmCmCmGmGmGmUm3'  (XVIII)

(wherein m represents an O-methyl-nucleotide unit, and other symbols represent deoxynucleotide units) from a methoxy derivative.

A cartridge was charged with 8 mg of controlled pore glass bounding 0.2 μmole of 5'-dimethoxytrityl-2'-O-methyl-uridine (compound IVc2) The cartridge was set in a DNA synthesizer model 380A (Applied Biosystems Co.) wherein an operation was repeatedly effected in 14 cycles according to the method shown in Table 6 by employing the following phosphoroamidites in this order: IIIb₂, IIIb₂, IIIb₂, Ib₂, Ib₂, IIIb₂, IIb₂, IVb₂, Ib₂, IVb₂, IId₂, IIId₂, IIId₂ and Id₂, to produce a protected mixed oligomer. According to the method shown in Table 3, the ammonia solution treated the polymer support was poured into 3 ml vial, and heated in a sealed state at 50° C. for 12 hours to remove the acyl group contained in the base. After cooling, the ammonia was removed, washed twice with 1 ml of ethyl acetate, and the aqueous layer was concentrated to dryness.

The residue thus obtained was dissolved in 200 μl of a 0.1 M acetic acid-triethylamine buffer solution containing 10% of acetonitrile, pH of 7.0 (TEAA), and subjected to a column chromatography employing a column (diameter: 1 cm, length: 10 cm) filled with a reversed phase silica gel (Prep PAK-500/C-18, Waters Company). As the mobile phase, 0.1 M TEAA (pH 7.0) with a concentration gradient ranging from 10 to 35% of acetonitrile was used. A quantitative analysis was performed by determining the light absorption at 254 nm. 2.2 OD-units of 5'-dimethoxytrityl-mixed oligonucleotide were isolated.

After the solvent had been removed from the reaction mixture by distillation under reduced pressure, the reaction mixture was treated with 1 ml of a 80% aqueous acetic acid solution, and kept at room temperature for 10 minutes. The solvent was distilled off under reduced pressure from the reaction solution, and the acetic acid component was removed by co-evaporation with water under reduced pressure.

The resultant residue was dissolved in water, and washed with ethyl acetate, and an aqueous phase was evaporated to dryness Then the reaction mixture was purified by means of high performance liquid chromatography, using a YMC pack ODS column (Yamamura Kagaku Co., Ltd.). As the mobile phase, a 0.1 M TEAA with a linear concentration gradient of 5 to 25% of acetonitrile (pH 7.0) was used.

The main peak, which had been eluted out at a flow velocity of 1 2 ml/minute, so that 0.91 OD-units (about 6 nmoles; yield: 3.0%) of the mixed oligo-nucleotide (XVIII) were obtained.

In a similar manner, the following products each were isolated.

| | | |
|---|---|---|
| 5'CGGATCmUmAmGmCmCmGmGmGmUm3' | (XVII) | (yield: 2.5%) |
| 5'CGGAmUmCmUmAmGmCmCmGmGmGmUm3' | (XIX) | (yield: 3.0%) |
| 5'AmCmAmCmAmCmCmCGGA3' | (XXII) | (yield: 6.8%) |
| 5'AmCmAmCmAmCmCmCGG3' | (XXIII) | (yield: 8.6%) |
| 5'CmUmCGAAAGmUm3' | (XXIV) | (yield: 3.2%) | tion mixture was washed twice with 1 ml of ethyl acetate, and the aqueous layer was concentrated to dryness.

The resulting residue was dissolved in 200 μl of a 0.1 M acetic acid-triethyl amine buffer solution containing 10% of acetonitrile (TEAA; pH 7.0). The solution thus obtained was subjected to a column chromatography using a column with a diameter of 1 cm and a length of 10 cm and filled with a reversed phase silica gel (Prep PAK-500/C-18, Waters Company). As the mobile phase, a 0.1 M TEAA with a linear concentration gradient ranging 10 to 35% of acetonitrile (pH 7.0) was used. 9.5 OD-units of the 5'-dimethoxytrityl-mixed oligomer was isolated by measuring the light absorption at 254 nm.

After the solvent was removed from the mixture by distillation under reduced pressure, 1 ml of a 80% aqueous acetic acid solution was added to the mixture, which was then kept at room temperature for 10 minutes. The reaction solution was subjected to distillation under reduced pressure to remove the solvent therefrom, and then co-evaporated with water under reduced pressure to remove the acetic acid. The residue was dissolved in water, washed with ethyl acetate, distilled under reduced pressure and purified by high performance liquid chromatography using a YMC pack column (Yamamura Kagaku Co., Ltd.). The mobile phase employed consisted of a 0.1 M TEAA with a linear concentration gradient ranging from 5 to 25% of acetonitrile (pH 7.0). The flow rate was 1 2 ml/minute. The main peak, which had been eluted out, was recovered, so that 1.9 OD-units (about 16 nmoles, yield: 8.1%) of the mixed oligo-nucleotide (XX) was obtained.

In a similar manner, the following mixed oligomer was obtained:

| | | |
|---|---|---|
| 5'AmCmAmCmAmCmCmCGGAT3' | (XXI) | (yield: 9.3%) |

EXAMPLE 15

Preparation of a mixed oligo-nucleotide of the formula

5'AmCmAmCmAmCmCmCGGAT3'  (XX)

(wherein m represents an o-methyl-nucleotide unit, and other symbols represent deoxynucleotide units) by using a β-cyanoethyl derivative A cartridge was charged with a controlled pore glass (Applied Biosystems Company) containing 0.2 μmole of 5'-dimethoxytrityl-thymidine bounded thereto. An operation was effected according to the method shown in Table 2 using the following phosphoroamidites in this order: IId₃, IIId₃, IIId₃, Ib₃, Ib₃, Ib₃, IIb₃, Ib₃, IIb₃, Ib₃ and IIb₃. Namely, the reaction operations were repeatedly carried out in 11 cycles, so that a protected mixed oligomer was synthesized.

Next, the oligomer was cut off from the polymer support (CPG) in the form of an ammonia solution according to the method shown in Table 3. A 3 ml vial was charged with the oligomer, sealed tightly, and heated to 50° C. for 9 hours to remove the β-cyanoethyl group and the acyl group of the base from the oligomer. After cooling, the ammonia was removed, and the reac-

EXAMPLE 16

Preparation of double chain DNA (XVI)

DNA-oligomers (1 to 9, chain length: 17 to 47) were synthesized by DNA auto-synthesizer using appropriate commercial compounds (Id₄ to IVd₄ and Id₂ to IVd₂) (ABI Company) and purified in a conventional manner.

1 nmole of each DNA-oligomer was admixed with 4 μl of a 0.5 M Tris-HCl (pH 7.5), 4 μl of a 0.1 M MgCl₂, 10 μl of a 0.2 nM of ATP, 4 μl of a 0.1 M DTT and 14 μl of H₂O. The resulting solution was then admixed with 2 μl (5 U) of T4-polynucleotide-kinase (Takara Shuzo Co., Ltd.), and subjected to a reaction operation at 37° C. for 40 minutes. Then to the reaction mixture, the same amount of the kinase was added, and again reacted for further 40 minutes.

A portion of the reaction mixture was admixed with a 5'-phosphorylated compound (1, 2, 5, 6) to form a "solution A", and another portion was admixed with a compound (3, 4, 7, 8, 9) to form a "solution B". These solutions were placed on a water bath at 80° C., and then cooled to 20° C. slowly for a period of time of 3 hours. To the solution A, 40 μl of a 2 mM ATP, 40 μl of a 0.1 M DTT and 1 μl (175 U) of T4-DNA ligase (Takara Shuzo Co., Ltd.), and the resulting mixture (100 μl) was subjected to a reaction operation at 15° C. for 20 hours. The solution B was admixed with 25 μl of a 2 mM ATP, 25 μl of a 0.1 M DTT and 0.5 μl (87 U) of ligase, and subjected to a reaction operation as in the case of the solution A.

Thereafter, these reaction solutions each were treated with phenol, and subjected to chromatography using a gel filtration column (SuperoseTE 6H10/30). The mobile phase consisted of a 0.05 M Tris-HCl and 1 mM EDTA (pH 8.0). The following products were obtained: the double chain A: 590 pmoles (1.07 OD); and the double chain B: 311 pmoles (0.62 OD).

347 pmoles of the chain A were mixed with 311 pmoles of the chain B, and the resulting mixture was admixed with 140 μl of the reaction solution (50 mM Tris-HCl, pH 7.5, 10 mM MgCl$_2$, 0.2 mM ATP and 10 mM DTT), and kept at 37° C. for 1 hour, annealed at room temperature, admixed with 0.5 μl (87 U) of T4-DNA ligase and subjected to a reaction operation at 15° C. for 1.5 hours. The reaction mixture was subjected to a phenol-chloroform treatment and to an ethanol precipitation treatment, and then concentrated to dryness under reduced pressure.

The resultant residue was mixed with 95 μl of a solution consisting of 6 mM Tris-HCl (pH 7.5), 6 mM MgCl$_2$, 125 mM NaCl and 7 mM DTT. The reaction solution was admixed with 5 μl (20 U) of SphI, and subjected to a reaction operation at 37° C. for 30 minutes, and to a reaction operation at room temperature for 2 days. The reaction mixture was subjected to a phenol-chloroform treatment and to an ethanol precipitation treatment, and then subjected to chromatography using a gel filtration column (SuperoseTH 6H10/30). After an ethanol precipitation treatment, 68 pmoles (7.6 μg) of the double DNA (XVI) were obtained.

EXAMPLE 17

Preparation of a vector for transcription, M13-AJ-1

2 μl of M13mp19 (0.1 μg/μl Takara Shuzo Co., Ltd.) were added to 20 μl of a solution containing 6 mM Tris-HCl (pH 7.5), 6 μl MgCl$_2$, 125 mM NaCl and 7 mM DTT. The resultant mixture was admixed with SphI (2 U; Takara Shuzo Co., Ltd.), and subjected to a reaction operation at 37° C. for 30 minutes. After a phenol-chloroform treatment and an ethanol precipitation treatment had been effected in a conventional manner, the reaction mixture was admixed with a 20 μl of solution containing 10 mM Tris-HCl (pH 8.0), 10 mM MgCl$_2$, 20 mM KCl and 7 mM DTT, and then admixed with SmaI (5 U: Takara Shuzo Co., Ltd.) to effect a reaction at 30° C. for 30 minutes.

After a phenol-chloroform treatment and an ethanol precipitation treatment had been carried out in a conventional manner, the reaction mixture was concentrated to dryness under reduced pressure. The resulting residue was added to a solution containing 50 mM Tris-HCl (pH 7.5), 10 mM MgCl$_2$, 0.2 mM ATP and 10 mM DTT. 0.04 μg of the double chain DNA, which is described in Example 16, and 2 U of T4-DNA ligase were added to the reaction mixture to effect a reaction at 16° C. for 3 hours. The reaction was further performed at 4° C. overnight. The resulting product (solution) was employed in the following transformation step in an amount of 1, 2 or 4 μl.

According to the known method disclosed in Method in Enzymology, 101, 20-78, 1983, a transformation of a competent cell of E. coli JM 103 was carried out, and a screening for white plaques was effected. From each of about 10 white plaques, a phage was taken out. The phage was added to 1.5 ml of a suspension containing E. coli JM 103, which suspension had been prepared by incubating the microorganism at 37° C. overnight and by diluting at a factor of 100. Then the microorganism was grown at 37° C. for 6 hours, and thereafter a centrifugal operation was effected at a speed of 12,000 rpm for 5 minutes, so that a clear supernatant layer was formed. A conventional treatment was carried out to obtain a single chain DNA, synthetic chain portion which had been inserted was sequenced, by a dideoxy method, so that the aimed clone was obtained.

100 μl of the above-mentioned supernatant phage solution were added to 1 liter of a JM 103 suspension (0.3 OD/570 nm), and an incubation operation was effected at 37° C. for 7 hours in a conventional manner, so that 445 μg of the aimed vector, M13AJ-1, were obtained

EXAMPLE 18

Preparation of WS-S(+)RNA

50 μg of M13-AJ-1 were added to 100 μl of a solution containing 70 units of SmaI (70 units), 10 mM Tris-HCl (pH 8.0), 10 mM MgCl$_2$, 20 mM KCl and 7 mM DTT to effect a reaction at 30° C. for 2 hours. The formation of a linear chain was confirmed with the aid of 1% agarose gel electrophoresis.

The reaction mixture was subjected to a phenol-chloroform treatment and then to an ethanol precipitation treatment, dissolved in 1 ml of water, and analysed by a UV light absorption at 260 nm (0.84 OD/ml; 42 μg).

The reaction mixture was again concentrated under a reduced pressure to dryness, and then dissolved in 84 μl of water. The resulting solution was used in the next transcription reaction.

According to the known method disclosed in Nucleic Acid Res., 12, 7035, 1984, a 1.5 ml eppen tube was charged with 5 μl each of 10 mM ATP, GTP, UTP and CTP, and the resulting mixture was admixed with 100 μl of [5-$^3$H]-UTP (100 μCi, 2.2×10$^8$ dpm/7.3 nmoles, Amasham Company), and concentrated under reduced pressure to dryness The residue thus obtained was mixed with 20 μl of a buffer for transcription (200 mM Tris-HCl (pH 7.5), 30 mM MgCl$_2$ and 10 mM spermidine), 10 μl of 100 mM DTT, 5 μl (150 U) of RNasin, 30 μl (15 μg) of the abovementioned SmaI cut DNA solution, 10 μl (150 U) of SP6-RNA polymerase and 25 μl of water (which had been treated with diethyl pyrocarbonate), so that 100 μl of the mixture was obtained.

The mixture was subjected to a reaction operation at 40° C. for 1 hour. Then the reaction mixture was admixed with 3 μl (45 U) of SP6-polymerase to react for 2 hours. The reaction solution was mixed with 15 μl (15 U) of RQIDNase and 4 μl (120 U) of RNasin to effect a reaction at 37° C. for 15 minutes. Thereafter, the reaction mixture was extracted once with 100 μl of a phenol-chloroform mixture and 100 μl of chloroform, then once with 100 μl of ethyl ether. After that, the mixture was concentrated to dryness. The agents used here were commercial chemicals sold as a kit from Promega Biotech. Company, except [³H] UTP supplied by Amasham Japan Co., Ltd.

The resulting residue was dissolved in 200 μl of water, treated with NENSORB20 (Du Pont Co.). 1 ml of the 50% methanol as an elute was concentrated under reduced pressure to dryness. The residue thus obtained was dissolved in 500 μl of a solution containing 10 mM Tris-HCl (pH 7.5) and 0.25 mM EDTA.

5 μl of the resultant solution was measured by a liquid scintillation counter (TRI-CARB 4640, Paccard Company). By this test, it was confirmed that the sample contained 3 μg of WS-S(+)-RNA. In addition, by an analysis using UV-spectroscopy at 260 nm, it was observed that the sample contained about 9 μg of DNA.

The WS-S(+)RNA solution, which had been obtained in this Example, was used in the next Example 19.

EXAMPLE 19

| Labelling of WS-S(+)RNA with 3'-$^{32}$PCp | |
|---|---|
| WS-S(+)RNA 336 ng (11.2 pmol) | 0.56 μM |
| [5'-$^{32}$P]pCp (Amasham Japan Co., Ltd.) 3000 Ci/mmol | 0.825 μM |
| ATP | 6 μM |
| HEPES (pH 8.3) | 50 mM |
| MgCl$_2$ | 10 mM |
| DTT | 3.3 mM |
| DMSO | 10% (v/v) |
| BSA | 10 μg/ml |
| glycerol | 15% (v/v) |
| RNA ligase (P. L. Pharmacia Company) at 45° C., for 16 hours | |
| total volume | 20 μl |

A reaction was carried out under the conditions shown above. The reaction mixture was heated to 65° C. for 5 minutes and then immediately cooled with ice before the additions of RNA ligase and [5'-$^{32}$P]pCp.

After the reaction had been completed, the reaction mixture was admixed with 20 μl of a loading solution containing 10% of urea and 0.02% of xylene cyanol and 0.02% of bromophenol blue, and then subjected to an electrophoresis operation, wherein the reaction mixtures were applied to a 8% polyacrylamide gel containing 7 M urea (length: 50 cm, and thickness: 0.5 mm), and the electrophoresis was done at 2,000 V for 2 hours. After this operation, the gel was subjected to autoradiography so that any one of the chains having a given length was separated from another one having a length shorter by one segment, and each chain was extracted from the gel according to the Maxam-Gilbert method. The extraction product is desalted with NENSORB™ (Du Pont Co.).

0.725 pmole of WS-S(+)RNA having a chain length different by one segment, which was labelled with 3'-$^{32}$PCp was obtained together with the same amount of the RNA having a chain length shorter by one segment (total amount: 1.45 pmoles, yield: 13%). Quantitative analysis was conducted on the basis of β-ray intensity measurement according to the Cerenkov method. The reaction mixture was mixed with H$_2$O in a concentration of 0.02 pmole/μl, and stored at a low temperature of −80° C. The WS-S(+)RNA labelled with $^{32}$PCp was employed in the next cleavage reaction.

EXAMPLE 20

| RNA chain cleavage reaction FIGS. 10-1 and 10-2 | |
|---|---|
| 3'-$^{32}$pCp-labelled WS-S(+)RNA | 3.3 nM |
| Mixed oligomer | 83 nM~8.3 μM |
| Tris-HCl (pH 7.7) | 40 mM |
| MgCl$_2$ | 4 mM |
| BSA | 0.003% |
| DTT | 1 mM |
| glycerol | 4% |
| RNaseH (Takara Shuzo Co., Ltd.) | 0.17~0.83 units/μl |
| total | 6 μl |

The mixture shown in the above table was heated to 65° C. for 2 minutes and annealed, before the RNaseH was added. The reaction was at 30° C., and was stopped at an appropriate time by adding 6 μl of a loading solution. Next, an electrophoresis of the mixture (2 μl) was carried out by using a 8% polyacrylamide gel containing 7 M of urea (thickness: 0.2 mm, length: 35 cm, 2,000 V, 2 hours).

Another reaction was conducted for 2 hours by using 8.3 μM of the mixed oligomer (this amount was 2500 times as large as the amount of RNA), and 0.17 unit/μl of the RNaseH. After that, an autoradiography operation was carried out with the aid of 8% PAGE. The result of this work is shown in FIG. 10-1.

In lane 8, a cleavage occurred between the 43rd G and the 44th A of the loop. In lane 10, a cleavage preferentially occurred between G$^{21}$ and G$^{22}$ in the stem. In lane 11, a cleavage occurred in each of two positions. In the DNA 44mer of lane 2, it was impossible to cleave site-specifically chain. In the complementary DNA 6mer of lane 3, no cleavage occurred.

FIG. 10-2 shows the result of a similar reaction, except that the amount of enzyme was 0.83 units/μl. In this case, cleavage occurred in lanes 6 and 7 due to the increase of enzyme employed.

In the experiment shown in FIG. 10-1, the electrophoresis was carried out without heating, whereas, in the experiment shown in FIG. 10-2, the electrophoresis was carried out under heating. In lanes 9, 10 and 11, it was observed that a change of the mobility which had occurred due to the structural change of RNA influenced by the mixed oligomer.

EXAMPLE 21

Figure 11:
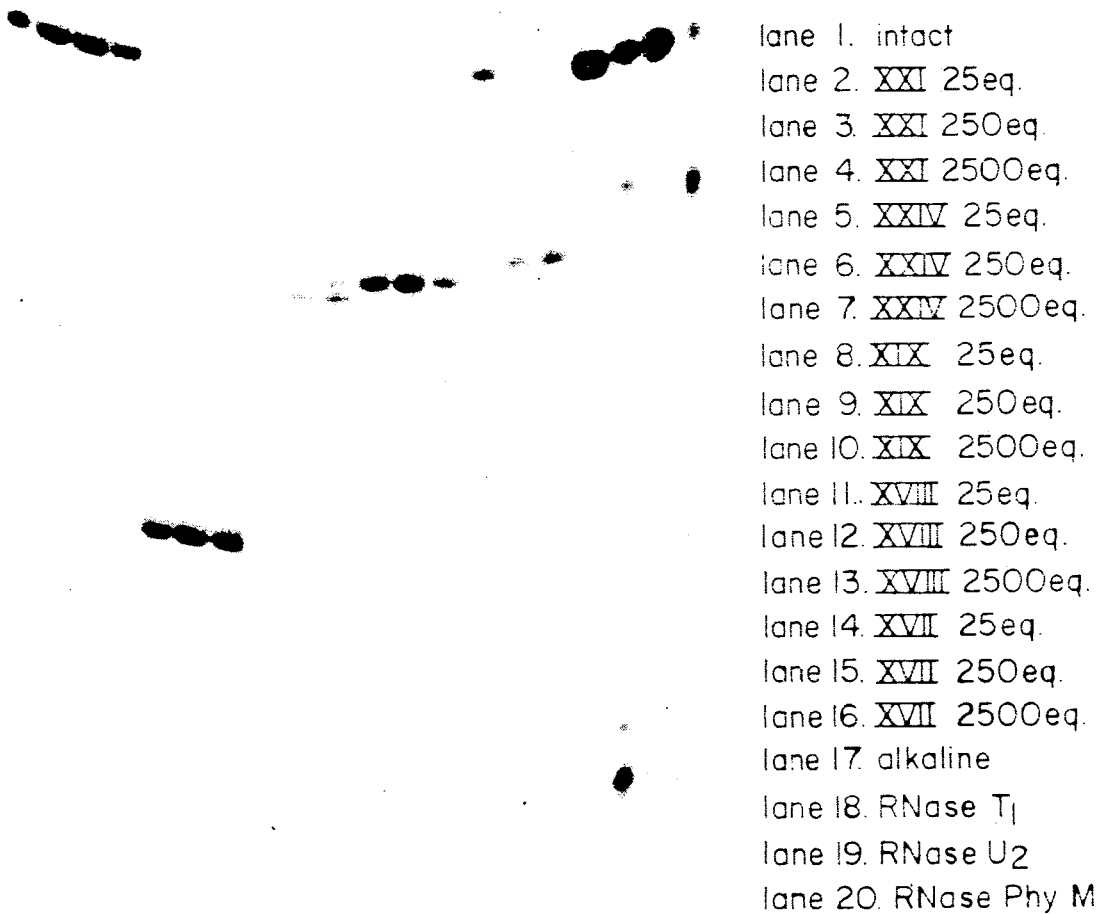

Experiment shown in FIG. 11

An experiment was carried out under virtually the same conditions as in Example 20, except that the amount of the mixed oligomer was decreased by a factor of 0.1 or 0.01 (the decreased amount was 25 or 250 times as large as the amount of RNA), and the amount of RNaseH employed was 0.42 unit/μl. The result of the experiment is illustrated in FIG. 11.

In lanes 5, 6 and 7 and lanes 11, 12 and 13, it was observed that, when the mixed oligomers (XXIV and XVIII) were used, a cleavage occurred and the starting material disappeared even if the amount used was 25 times as large as the amount of RNA. Thus, cleavages occurred between G$^{21}$ and G$^{22}$ and between G$^{22}$ and G$^{23}$. On the other hand, when the mixed oligomer (XXI) was used, a cleavage slightly occurred between G$^{21}$ and G$^{22}$, with the proviso that the amount employed was 2500 times as large as the amount of RNA.

EXAMPLE 22

Preparation of RNA chain length marker

In this experiment, a 3'-$^{32}$PCp-labelled WS-S(+)RNA having 30,000 to 60,000 cpm was used, and an Expanded RNA Sequencing Kit (Pharmacia Company), and an RNaseT$_1$ (Sankyo Co., Ltd.). Reactions were carried out in a conventional manner. 2 μl of the reaction solutions were subjected to an electrophoresis operation.

In the alkali hydrolysis reaction, 1 μl of WS-S(+)RNA labelled by $^{32}$P at 3'-terminal and 1 μl of carrier tRNA (2 μf/μl) were admixed with 1 μl of a CO$_3$/HCOhd 3 solution, and the resulting solution was heated to 90° C. for 6 minutes and then cooled on ice. The mixture was thereafter mixed with 3 μl of a urea-dye solution containing 5 mM Tris-HCl, 5 mM boric acid, 1 mM EDTA, 0.01% xylene cyanol FF, 0.01% bromophenol and 10 M urea. A portion (2 μl) of the resultant mixture was used in an electrophoresis operation.

In the RNaseT$_1$ digestion reaction, 1 μl of WS-S(+)RNA labelled by $^{32}$P in 3'-terminal (about 50,000 cpm) was mixed with 3 μl of a buffer solution (which contained 33 mM sodium citrate (pH 5.0), 1.7 mM EDTA, 0.04% xylene cyanol FF, 0.08% bromophenol blue, 1 mg/ml carrier tRNA and 7 M urea), 1 μl of distilled water and 1 μl of RNaseT$_1$ (0.01 unit/μl, Sankyo Company), to effect a reaction at 55° C. for 12 minutes. Thereafter, the reaction mixture was cooled on ice, and a portion (2 μl) of the mixture was subjected to an electrophoresis operation.

In the RNaseU$_2$ digestion reaction, 1 μl of WS-S(+)RNA labelled with $^{32}$P at 3'-terminal (about 50,000 cpm) was mixed with 3 ||1 of a buffer solution (33 mM sodium citrate (pH 3.5), 1.7 mM EDTA, 0.04% xylene cyanol FF, 0.08% bromophenol blue, 1 mg/ml carrier tRNA and 7 M urea), 1 μl of distilled water, and 1 μl of RNaseU$_2$ (2 units/μl, Pharmacia Company), to effect a reaction at 55° C. for 12 minutes. After the reaction, the reaction mixture was cooled on ice, and a portion (2 μl) of the mixture was subjected to an electrophoresis operation.

EXAMPLE 23

Analysis of 5'-terminal base of RNase cleaved product (i.e. the product wherein the 5'CmUmCGAAAG-mUm3'(XXIV) has been used)

0.02 pmole (about 200 cpm, measured by the Cerenkov method) of WS-S(+)RNA labelled with $^{32}$PCp at 3'-terminal was cleaved with the aid of 5'CmUmC-GAAAGmUm3'and RNaseH. 6 μl of the reaction solution of this cleavage reaction was admixed with 200 μl of a solution A (which comprised 0.1 M Tris-HCl, 10 mM triethylamine and 1 mM EDTA (pH 7.7)), and the mixture thus formed was placed in a cartridge for the purification of nucleic acids (NENSORB$^{TM}$ 20, Du Pont Company). The sample was washed with 3 ml of solution A and then with 1 ml of distilled water, and eluted out by 500 μl of 50% aqueous methanol. The effluent was concentrated under reduced pressure to dryness.

The eluent was used to effect a reaction of exchanging the 5'-terminal phosphatate by $^{32}$P having a high specific activity according to the known method disclosed in The Journal of Biological Chemistry, 252, 3176–3184, 1977. In this operation, the effluent was admixed with 1 μl of 0.5 M imidazole-hydrochloric acid buffer solution, 1 μl of 0.1 M magnesium chloride, 1 μl of 1 mM spermidine, 1 μl of 1 mM EDTA, 1 μl of 50 mM dithiothreitol, 2 μl of distilled water and 1 μl of 3 mM ADP, and the mixture thus formed was heated to 65° C. for 2 minutes, and then immediately cooled on ice.

The mixture was supplied to a vessel, which already contained [γ-$^{32}$P]ATP (20 pmoles, 100 μCi, Amasham Japan Co., Ltd.) which had been concentrated to dryness. 1 μl of T4-polynucleotide kinase (7 units/μl, Takara Shuzo Co., Ltd.) were added to the mixture, and a reaction was performed at 37° C. for 30 minutes. Then the reaction solution was admixed with 10 μl of a solution containing 10 M urea, 0.02% xylene cyanol and 0.02% bromophenol blue. The whole amount of the mixture was subjected to an electrophoresis (2,000 V, 2 hours) employing 8% polyacrylamide gel which contained 7 M urea (thickness: 0.2 mm; length: 35 cm). After the electrophoresis, an autoradiography operation was carried out to separate a band of the chain having about 48 nucleotides in length. Then the sample was finely crushed, and admixed with 300 μl of a solution containing 0.5 M ammonium acetate and 0.1 mM EDTA, and the resulting mixture was kept at room temperature for 1 day. The gel was separated by a centrifugal operation, and the filtrate was concentrated under reduced pressure to dryness. The 48th chain fraction thus obtained was mixed with 200 μl of a solution A (which contained 0.1 M Tris-HCl, 10 mM triethylamine and 1 mM EDTA, pH 7.7), and then with 4 μg of a carrier tRNA.

The resultant mixture was thereafter applied to a cartridge for the nucleic acid purification (NENSORB$^{TM}$ 20, Du Pont Company), washed with 3 ml of the solution A and then with 1 ml of distilled water, and an elution was carried out with the aid of 500 μl of a 50% aqueous methanol. The effluent (800 cpm, determined according to the Cerenkov method) was concentrated under reduced pressure to dryness, admixed with 8 μl of distilled water, 1 μl of 0.4 M ammonium acetate (pH 5.0) and a nuclease P1 (0.1 μg/1 μl, Yamasa Shoyu Co., Ltd.) to effect a reaction at 37° C. for 30 minutes.

The reaction solution was spotted onto a filter paper No. 51 (40 cm), and a paper electrophoresis operation was effected in the presence of 0.2 M morpholine acetate buffer solution (pH 3.5) at 900 V and 3.5 mA for 90 minutes. The samples were 5'CMP, 5'AMP, 5'GMP, 5'UMP, and 3'-terminal $^{32}$PCp-labelled yeast 5SRNA digestion product by nuclease P1 obtained under the same conditions.

After the electrophoresis, a radioautography operation was carried out. In this test, 5'AMP was found in the sample as shown in FIG. 12-A. From the above, it ca be said that the cleavage occurred between the 43rd G and the 44th A.

Furthermore, the cleavage products prepared by employing the compounds (XVII) and (XVIII), were tested in a similar manner. Namely, each of $^{32}$PCp-labelled WS-S(+)RNA was employed in an amount of about 0.02 pmol (about 1,000 cpm, determined according to the Cerenkov method) for the analysis of the 5'-terminal group. The cleaved products containing 5'-terminal phosphate exchanged by $^{32}$P with a high specific activity, were isolated in amounts of 3300 cpm (the cleaved product of compound (XVII)) and 4800 cpm (the cleaved product of compound (XVIII)).

These were completely digested with a nuclease P1, and then subjected to an acidic paper electrophoresis operation and thereafter to a radioautography operation. The results of the tests are illustrated in FIG. 12-B. In each case, the 5'-terminal was G. In consideration of the chain length marker (FIG. 10-2), it can be concluded that a cleavage occurred between $C^{20} \underline{\downarrow} G^{21'}$ of XVIII and between $G^{21} \underline{\downarrow} G^{22}$ of XVIII.

EFFECTS AND ADVANTAGES OF THE INVENTION

As explained in the preceding paragraphs, it is possible according to the invention to preferentially cleave at a specific position of an RNA molecule independent of the chain length of the molecule. Therefore, it is believed that if the invention is employed, then various studies on the structures and the functions of various kinds of RNA will be conducted more easily. Furthermore, it is expected that the invention may be utilized, for instance, in the mass production of useful proteins.

It is to be noted that (1) E.coli JM 103, (2) vector M13AJ-1, and (3) E.coli HB101 referred to above are available to the public.

TABLE 1

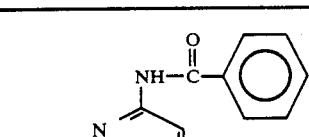

| | | | |
|---|---|---|---|
| I | X = H, | Y = H, | Z = OCH$_3$ |
| Ia | X = DMTr | Y = H | Z = OCH$_3$ |
| Ib$_1$ | X = DMTr | Y = R$_1$ | Z = OCH$_3$ |
| Ic$_1$ | X = DMTr | Y = (P$_1$) | Z = OCH$_3$ |
| Id$_1$ | X = DMTr | Y = R$_1$ | Z = H |

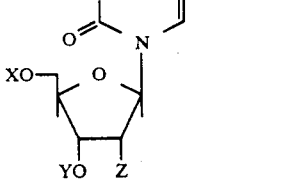

| | | | |
|---|---|---|---|
| II | X = H | Y = H | Z = OCH$_3$ |
| IIa | X = DMTr | Y = H | Z = OCH$_3$ |
| IIb$_1$ | X = DMTr | Y = R$_1$ | Z = OCH$_3$ |
| IIc$_1$ | X = DMTr | Y = (P$_1$) | Z = OCH$_3$ |
| IId$_1$ | X = DMTr | Y = R$_1$ | Z = H |

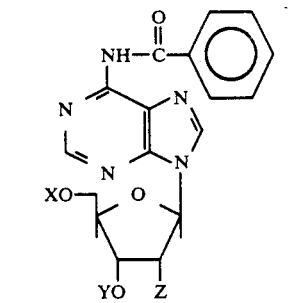

| | | | |
|---|---|---|---|
| III | X = H | Y = H | Z = OCH$_3$ |
| IIIa | X = DMTr | Y = H | Z = OCH$_3$ |
| IIIb$_1$ | X = DMTr | Y = P$_1$ | Z = OCH$_3$ |
| IIIc$_1$ | X = DMTr | Y = R$_1$ | Z = OCH$_3$ |
| IIId$_1$ | X = DMTr | | Z = H |

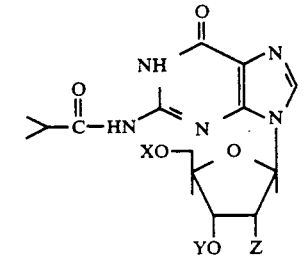

| | | | | |
|---|---|---|---|---|
| IV | X = H | Y = H | Z = OCH$_3$ | R' = H |
| IVa | X = DMTr | Y = H | Z = OCH$_3$ | R' = H |
| IVb$_1$ | X = DMTr | Y = R$_1$ | Z = OCH$_3$ | R' = H |
| IVc$_1$ | X = DMTr | Y = (P$_1$) | Z = OCH$_3$ | R' = H |
| IVd$_1$ | X = DMTr | Y = R$_1$ | Z = H | R' = CH$_3$ |

TABLE 1-continued

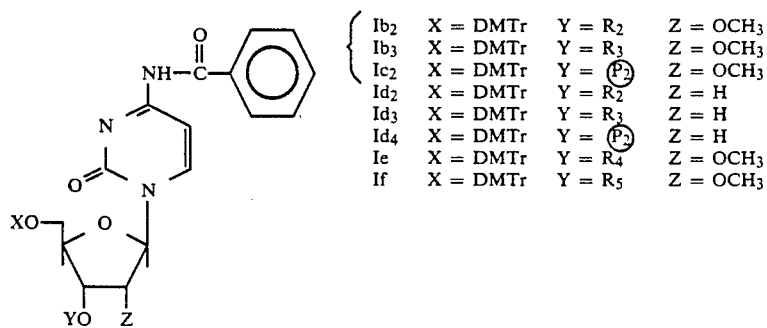

| | X | Y | Z |
|---|---|---|---|
| Ib₂ | DMTr | R₂ | OCH₃ |
| Ib₃ | DMTr | R₃ | OCH₃ |
| Ic₂ | DMTr | (P₂) | OCH₃ |
| Id₂ | DMTr | R₂ | H |
| Id₃ | DMTr | R₃ | H |
| Id₄ | DMTr | (P₂) | H |
| Ie | DMTr | R₄ | OCH₃ |
| If | DMTr | R₅ | OCH₃ |

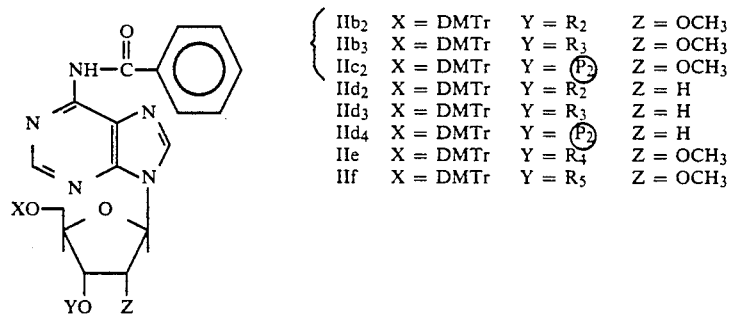

| | X | Y | Z |
|---|---|---|---|
| IIb₂ | DMTr | R₂ | OCH₃ |
| IIb₃ | DMTr | R₃ | OCH₃ |
| IIc₂ | DMTr | (P₂) | OCH₃ |
| IId₂ | DMTr | R₂ | H |
| IId₃ | DMTr | R₃ | H |
| IId₄ | DMTr | (P₂) | H |
| IIe | DMTr | R₄ | OCH₃ |
| IIf | DMTr | R₅ | OCH₃ |

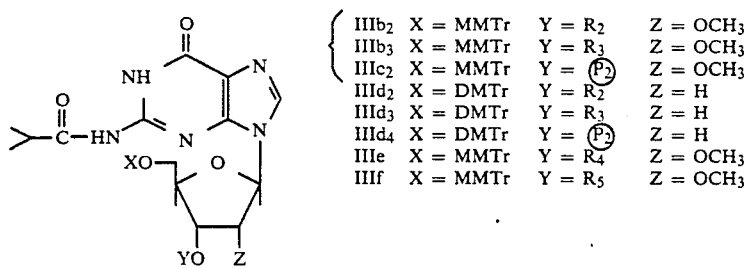

| | X | Y | Z |
|---|---|---|---|
| IIIb₂ | MMTr | R₂ | OCH₃ |
| IIIb₃ | MMTr | R₃ | OCH₃ |
| IIIc₂ | MMTr | (P₂) | OCH₃ |
| IIId₂ | DMTr | R₂ | H |
| IIId₃ | DMTr | R₃ | H |
| IIId₄ | DMTr | (P₂) | H |
| IIIe | MMTr | R₄ | OCH₃ |
| IIIf | MMTr | R₅ | OCH₃ |

TABLE 1-continued

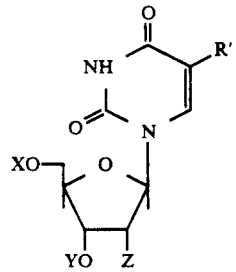

| | | | | |
|---|---|---|---|---|
| IVb$_2$ | X = DMTr | Y = R$_2$ | Z = OCH$_3$ | R' = H |
| IVb$_3$ | X = DMTr | Y = R$_3$ | Z = OCH$_3$ | R' = H |
| IVc$_2$ | X = DMTr | Y = (P$_2$) | Z = OCH$_3$ | R' = H |
| IVd$_2$ | X = DMTr | Y = R$_2$ | Z = H | R' = CH$_3$ |
| IVd$_3$ | X = DMTr | Y = R$_3$ | Z = H | R' = CH$_3$ |
| IVd$_4$ | X = DMTr | Y = (P$_2$) | Z = H | R' = CH$_3$ |
| IVe | X = DMTr | Y = R$_4$ | Z = OCH$_3$ | R' = H |
| IVf | X = DMTr | Y = R$_5$ | Z = OCH$_3$ | |

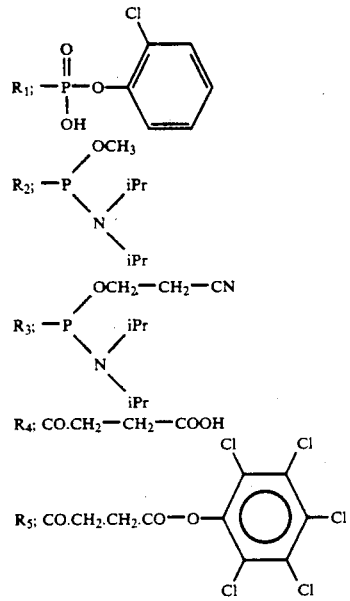

R$_4$; CO.CH$_2$—CH$_2$—COOH

R$_5$; CO.CH$_2$.CH$_2$.CO—O—[2,3,4,5,6-pentachlorophenyl]

P$_1$ : 1% of the divinylbenzene polystyrene resin combined with spacer
(P$_2$): Combined long chain alkylamino controlled pore glass through spacer

TABLE 2

A cycle of the operation for the chain elongation reaction

| Operation Number | Description | Volume Operation number | Time |
|---|---|---|---|
| 1 | Dichloromethane-Methanol (7:3) washing | 2 ml × 3 | |
| 2 | Benzene sulfonic Acid/Dichloromethane-Methanol (7:3) | 2 ml | 1 min |
| 3 | Dichloromethane-Methanol (7:3) washing | 2 ml | |
| 4 | 2% Benzenesulfonic Acid/Dichloromethane-Methanol (7:3) | 2 ml | 1 min |
| 5 | Dichloromethane-Methanol (7:3) washing | 2 ml × 2 | |
| 6 | Pyridine washing | 2 ml × 3 | |
| 7 | Pyridine co-evaporation | 0.3 ml | |
| 8 | 2'-O-methylnucleotide/pyridine | 2.0 mg × 0.3 ml | co-evaporation |
| 9 | Mesitylenesulfonyl-3-nitrotriazolide/pyridine(coupling) | 2.0 mg × 0.3 ml | 20 min (40° C.) |
| 10 | Pyridine washing | 2 ml × 2 | |
| 11 | 0.1 M Dimethylaminopyridine/Pyridine<br>Acetic anhydride | 1.8 ml<br>0.2 ml | 3 min |
| 12 | Pyridine washing | 2 ml × 3 | |

TABLE 3

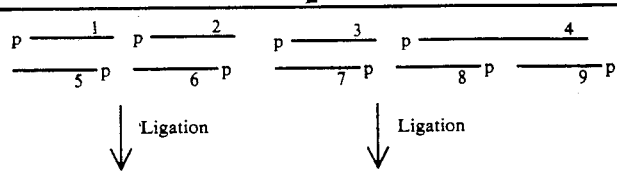

TABLE 3-continued
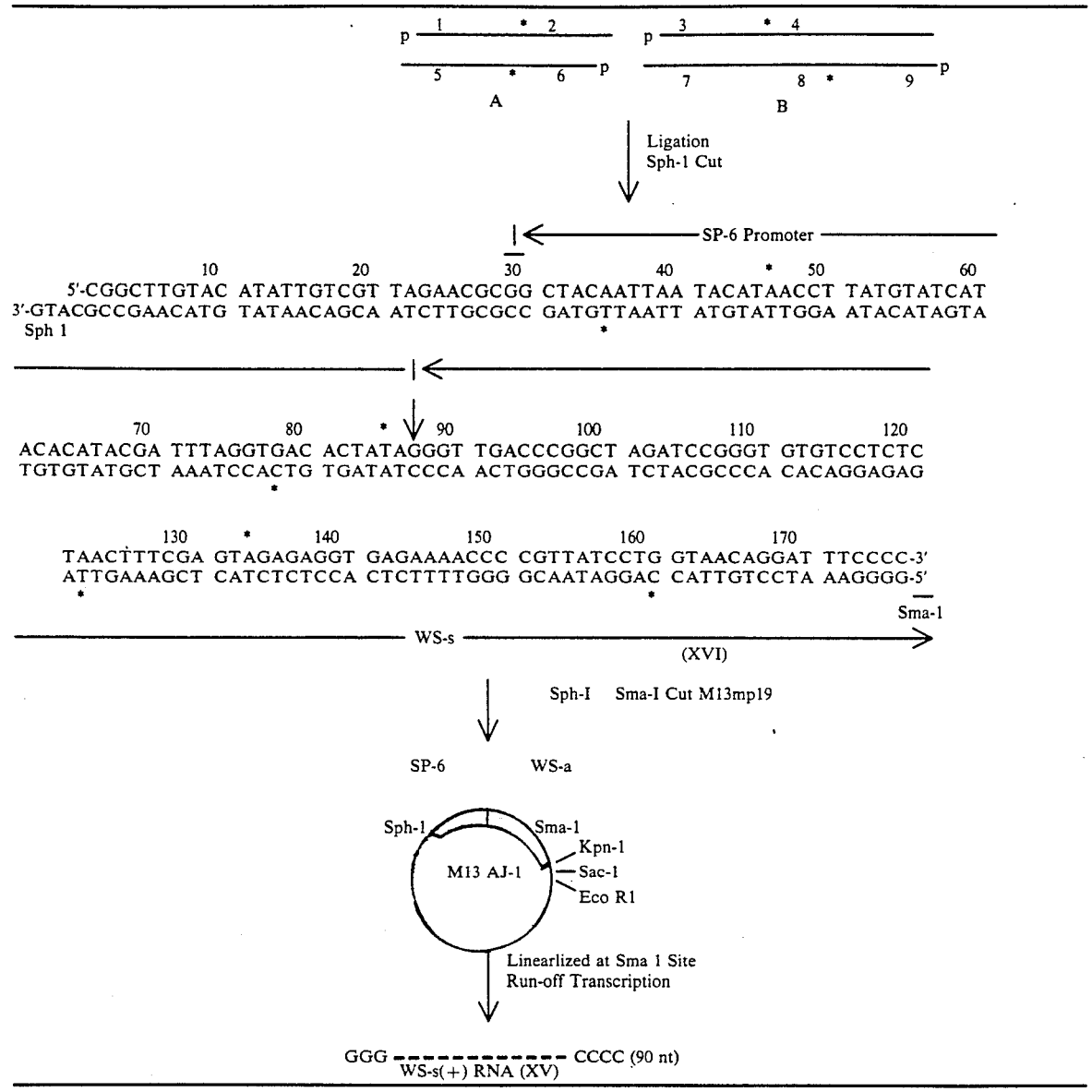
TABLE 4
```
    1    5    10   15   20   25   30   35   40   45
5'                                                  3'
pppGGGUUGACCCGGCUAGAUCCGGGUGUGUCCUCUCUAACUUUCGAGU
```
(XVII)  3'————TAGGC5'
(XVIII) 3'————AGGC5'
(XIX)   3'————GGC5'
(XX)    3'TAGG————5'
(XXI)   3'TAGGC————5'
(XXII)  3'AGGC————5'
(XXIII) 3'GGC————5'
(XXIV)  3'-AAAGC-5'
2'-O—Me—RNA: shown by the solid line

TABLE 4-continued

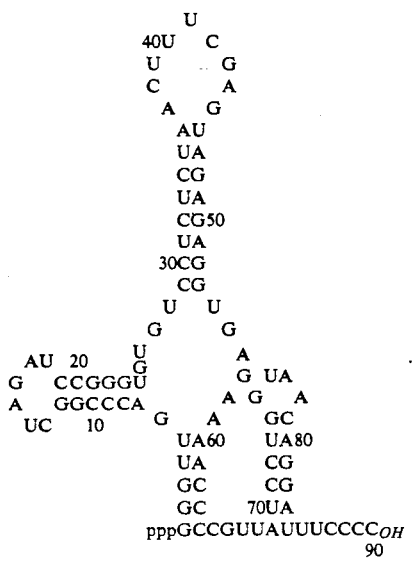

The nucleotide sequences of mixed oligomers complementary to WS-S(+)RNA, and the structure of WS-S(+) RNA.

TABLE 5

The cleavage sites using each mixed oligomer

```
          1    5    10   15   20   25
                              ↓↓
5'pppGGGUUGACCCGGCUAGAUCCGGGUGU3'
   XVII 3'——————————TAGGC5'
```

```
          1    5    10   15   20   25
                                ↓
5'pppGGGUUGACCCGGCUAGAUCCGGGUGU3'
   XVIII 3'——————————AGGC5'
```

```
          1 .  5    10   15   20   25
                              ↓↓
5'pppGGGUUGACCCGGCUAGAUCCGGGUGU3'
   XIX  3'——————————GGC5'
```

```
          1    5    10   15   20   25   30
                              ↓↓
5'pppGGGUUGACCCGGCUAGAUCCGGGUGUGUCCUC3'
    XX           3'  TAGG—————————5'
```

```
          1    5    10   15   20   25   30
                                ↓
5'pppGGGUUGACCCGGCUAGAUCCGGGUGUGUCCUC3'
   XXI           3'  TAGGC————5'
```

```
          1    5    10   15   20   25   30
5'pppGGGUUGACCCGGCUAGAUCCGGGUGUGUCCUC3'
   XXII                    AGGC———
                       3'           5'      ——→not cleaved
   XXIII                    GGC———
```

```
         30   35   40   45
                        ↓↓
5'GUCCUCUCUAACUUUCGAGU3'
   XXIV 3'——AAAGC——5'
```

↓ The arrows indicate the cleavage sites
2'—O—Me—RNA: shown by solid line

TABLE 6

A cycle of the operation for the chain elongation reaction
(using 0.2 μM CPG resin)

| | Time (sec), operation number | |
|---|---|---|
| Description | Methoxy-Phosphoramidite | β-cyanoethyl-phosphoramidite |
| CH₃CN washing | 20 | 20 |
| Ar drying | 5 | 5 |
| 3% CCl₃COOH/CH₂Cl₂ | 50 | 50 |
| CH₃CN washing | 30 ⎫ ×2 | 30 ⎫ ×2 |
| Ar drying | 5 ⎭ | 5 ⎭ |
| CH₃CN washing | 60 | 40 |
| Ar drying | 20 | 20 |
| Phosphoroamidite/tetrazole/CH₃CN | 5 | 5 |
| wait | 33 | 43 |
| Ar drying | 5 | 5 |
| Ac₂O-DMAP-luthidine/THF | 10 | 10 |
| wait | 120 | 11 |
| Ar drying | 5 | 10 |
| CH₃CN washing | 15 | 15 |
| Ar drying | 5 | 5 |
| I₂-H₂O-luthidine-THF | 15 | 15 |
| wait | 30 | 30 |
| Ar drying | 20 | 20 |
| CH₃CN washing | 10 ⎫ ×4 | 10 ⎫ ×4 |
| Ar drying | 5 ⎭ | 5 ⎭ |

TABLE 7

Deprotection and Cleavage operations from CPG resin
(Using 0.2 μM CPG resin)

| | | Time (sec), operation numbers | |
|---|---|---|---|
| Description | | Methoxy-Phosphoramidite | β-cyanoethyl-phosphoramidite |
| Ar drying | | 60 | 20 |
| PhSH-Et₃N-dioxane | | 40 | |
| wait | | 1 hr | |
| Ar drying | | 20 | |
| MeOH washing | | 50 ⎫ ×3 | |
| Ar drying | | 60 ⎭ | |
| Conc.NH₃ | (The solution which treated CPG resin was collected into the vial from this operation.) | 18 ⎫ ×4 ⎪ 15 min ⎭ | 15 ⎫ ×4 ⎪ 15 min ⎭ |
| Ar drying | ↓ | 15 | 15 |
| Conc.NH₃ | ↓ | 15 | 15 |
| Ar drying | ↓ | 15 | 15 |

We claim:

1. A compound having a double chain and which is composed of an RNA (+chain) and a complementary DNA (−chain), wherein at least one portion of said DNA (−chain) has been replaced by a 2′-O-substituted RNA, wherein said 2′-O-substituted RNA has at least one substituted 2′-hydroxyl group on the ribose moieties of said 2′-O-substituted RNA, and wherein, when said compound is subjected to the action of an enzyme having ribonuclease H activity, the RNA (+chain) is cleaved at a position corresponding to the unreplaced portion of the DNA (−chain).

2. The compound of claim 1, wherein said 2′-O-substituted RNA is substituted on at least one 2′-hydroxyl group of the ribose moieties of the RNA by a methyl group.

3. The compound of claim 1, wherein said 2′-O-substituted RNA is substituted on all hydroxyl groups of the ribose moieties of the RNA by a methyl group.

4. The compound of claim 1, wherein said 2′-O-substituted RNA is substituted on at least one 2′-hydroxyl group of the ribose moieties of the RNA by an ethyl group.

5. The compound of claim 1, wherein said 2′-O-substituted RNA is substituted on at least one 2′-hydroxyl group of the ribose moieties of the RNA by a propyl group.

6. A mixed oligomer which comprises a 2′-O-substituted RNA oligomer and a DNA oligomer, wherein said 2′-O-substituted RNA oligomer has at least one substituted 2′-hydroxyl group on the ribose moieties of said 2′-O-substituted RNA oligomer, wherein said 2′-O-substituted RNA oligomer is conjugated to said DNA oligomer via a phosphodiester linkage between the 5′-hydroxyl group and the 3′-hydroxyl group in the ribose or deoxyribose moiety.

7. The mixed oligomer of claim 6, wherein said 2′-O-substituted RNA oligomer is substituted on at least one 2′-hydroxyl group of the ribose moieties of the RNA by a methyl group.

8. The mixed oligomer of claim 6, wherein said 2′-O-substituted RNA oligomer is substituted on all 2′-hydroxyl groups of the ribose moieties of the RNA by a methyl group.

9. The mixed oligomer of claim 6, wherein said 2′-O-substituted RNA oligomer is substituted on at least one 2'-hydroxyl group of the ribose moieties of the RNA by an ethyl group.

10. The mixed oligomer of claim 6, wherein said 2'-O-substituted RNA oligomer is substituted on at least one 2'-hydroxyl group of the ribose moieties of the RNA by a propyl group.

11. A nucleoside compound of the formula:

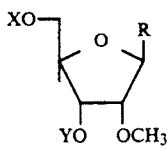

wherein X is a monomethoxy-trityl or dimethoxy-trityl radical, Y represents —P(OCH₃)—N—(CH(CH₃)₂)₂, —P(OCH₂CH₂CN)—N—(CH(CH₃)₂)₂, or —CO(CH₂-)ₘ—CO—NH—(CH₂)ₙ-(CPG), *m and n are each an integer of* 1 to 10, and R represents a radical of one of the formulae:

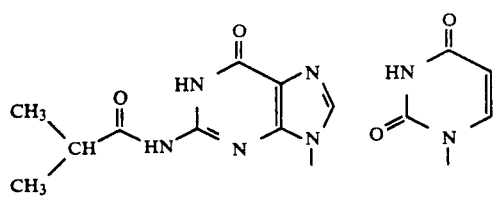

12. The nucleoside compound of claim 11, wherein R is:

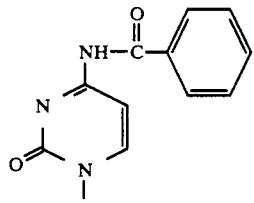

13. The nucleoside compound of claim 11, wherein R is:

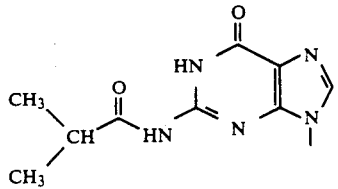

14. The nucleoside compound of claim 11, wherein R is:

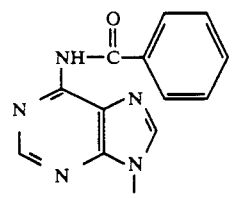

15. The nucleoside compound of claim 11, wherein R is:

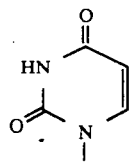

16. A mixed oligomer which comprises a 2'-O-substituted RNA oligomer and a DNA oligomer, wherein the 2'-O-substituted RNA is conjugated to the DNA oligomer via a phosphodiester linkage between the 5'-hydroxyl group and the 3'-hydroxyl group in the ribose or deoxyribose moiety, wherein the DNA oligomer is from 3 to 6 bases long.

17. The mixed oligomer of claim 16, wherein at least one, and up to all, of the 2'-hydroxyl groups in the sugar portion of the RNA has a substituent.

* * * * *